United States Patent [19]

Stokbroekx et al.

[11] Patent Number: 5,070,090
[45] Date of Patent: Dec. 3, 1991

[54] ANTIPICORPAVIRAL HERTEROCYCLIC-SUBSTITUTED MORPHOLINYL ALKYLPHENOL ETHERS

[75] Inventors: Raymond A. Stokbroekx, Beerse; Marcel J. M. Van der Aa, Kasterlee, both of Belgium

[73] Assignee: Janssen Pharmaceutica N.V., Beerse, Belgium

[21] Appl. No.: 514,635

[22] Filed: Apr. 25, 1990

Related U.S. Application Data

[63] Continuation-in-part of Ser. No. 351,699, May 15, 1989, abandoned.

[51] Int. Cl.$^5$ ............................................ C07D 413/02
[52] U.S. Cl. ............................ 514/236.5; 514/228.2; 514/235.2; 514/236.8; 514/252; 544/60; 544/62; 544/114; 544/133; 544/134; 544/367; 544/368; 544/369
[58] Field of Search ................ 544/114, 238, 237, 133, 544/134; 514/236.5, 235.2, 236.8

[56] References Cited

U.S. PATENT DOCUMENTS

| | | | |
|---|---|---|---|
| 2,562,036 | 7/1951 | Hultquist et al. | 544/238 |
| 2,985,657 | 5/1961 | Janssen | 544/238 |
| 3,631,043 | 12/1971 | Regnier et al. | 544/238 |
| 4,101,660 | 7/1978 | Inoue et al. | |
| 4,353,904 | 10/1982 | Thieme et al. | 544/364 |
| 4,451,476 | 5/1984 | Diana | 548/247 |
| 4,590,196 | 5/1986 | Smith et al. | 514/253 |
| 4,861,791 | 8/1989 | Diana et al. | 514/374 |
| 4,891,375 | 1/1990 | Lowe, III | 514/252 |
| 4,942,241 | 7/1990 | Diana et al. | 548/131 |
| 4,992,433 | 2/1991 | Stokbroekx et al. | 544/238 |
| 5,001,125 | 3/1991 | Stokbroekx et al. | 544/238 |

FOREIGN PATENT DOCUMENTS

| | | |
|---|---|---|
| A-0137242 | 4/1985 | European Pat. Off. . |
| A-0207453 | 1/1987 | European Pat. Off. . |
| A-0207454 | 1/1987 | European Pat. Off. . |
| A-211157 | 2/1987 | European Pat. Off. . |
| A-0211457 | 2/1987 | European Pat. Off. . |
| 0320032 | 6/1989 | European Pat. Off. ............ 544/238 |
| 2432005 | 2/1915 | Fed. Rep. of Germany . |
| A-3819037 | 12/1989 | Fed. Rep. of Germany . |
| A-3825170 | 1/1990 | Fed. Rep. of Germany . |
| 0077866 | 5/1983 | Japan ................................ 544/114 |
| 20-83375 | 9/1988 | Japan . |

OTHER PUBLICATIONS

Loftus, Synthetic Communications, vol. 10, No. 2, pp. 59-72 (1980).
J. Med. Chem., 15(3) (295-301).

*Primary Examiner*—Donald Daus
*Attorney, Agent, or Firm*—Charles J. Metz

[57] ABSTRACT

Novel (thio)morpholinyl and piperazinyl alkylphenol ethers having antirhinoviral activity, compositions containing these compounds as active ingredient, and a method of inhibiting, combating or preventing the growth of viruses in warm-blooded animals suffering from diseases caused by these viruses.

23 Claims, No Drawings

ANTIPICORPAVIRAL HERTEROCYCLIC-SUBSTITUTED MORPHOLINYL ALKYLPHENOL ETHERS

CROSS-REFERENCE TO RELATED APPLICATION

This is a continuation-in-part of our copending application Ser. No. 351,699, filed May 15, 1989, now abandoned.

BACKGROUND OF THE INVENTION

In EP-A-0,156,433 there are described antivirally active pyridazinamines. Further antiviral agents are described in U.S. Pat. No. 4,451,476, EP-A-0,137,242 and EP-A-0,207,453.

The compounds of the present invention differ from the cited art compounds by the fact that they contain a (thio)morpholinyl or piperazinyl moiety which is substituted in a previously undisclosed manner and particularly by their favourable antirhinoviral properties.

DESCRIPTION OF THE INVENTION

The present invention is concerned with (thio)morpholinyl and piperazinyl alkylphenol ethers of formula

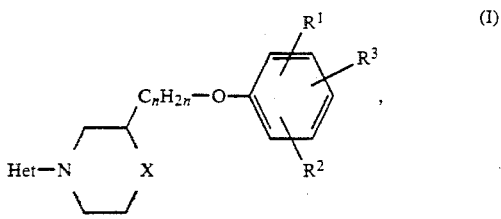

the addition salts thereof and the stereochemically isomeric forms thereof, wherein
Het is a heterocycle of formula

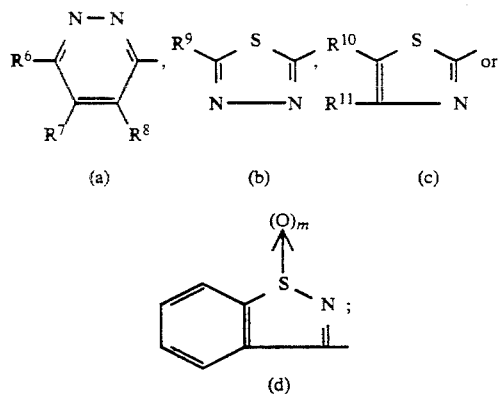

$R^6$ is hydrogen, $C_{1-4}$alkyl, halo, hydroxy, trifluoromethyl, cyano, $C_{1-4}$alkyloxy, $C_{1-4}$alkylthio, $C_{1-4}$alkylsulfinyl, $C_{1-4}$alkylsulfonyl, $C_{1-4}$alkyloxycarbonyl, $C_{1-4}$alkylcarbonyl or aryl;
$R^7$ and $R^8$ each independently are hydrogen or $C_{1-4}$alkyl;
$R^9$ is hydrogen, halo, amino, $C_{1-4}$alkyl, trifluoromethyl or aryl;
$R^{10}$ is hydrogen, halo, amino or nitro;
$R^{11}$ is hydrogen, $C_{1-4}$alkyl, $C_{1-4}$alkyloxycarbonyl or aryl;

m is 0, 1 or 2;
X is O, S or $NR^5$ with $R^5$ being hydrogen, $C_{1-4}$alkyl or aryl$C_{1-4}$alkyl;
n is an integer of from 1 to 4 inclusive;
$R^1$ and $R^2$ each independently are hydrogen, $C_{1-4}$alkyl or halo; and
$R^3$ is hydrogen, halo, cyano, $C_{1-4}$alkyloxy, aryl or —$COOR^4$ with $R^4$ being hydrogen, $C_{1-4}$alkyl, aryl$C_{1-4}$alkyl, $C_{3-6}$cycloalkyl$C_{1-4}$alkyl, $C_{3-5}$alkenyl, $C_{3-5}$alkynyl or $C_{1-4}$alkyloxy$C_{1-4}$alkyl; or $R^3$ is a radical of formula

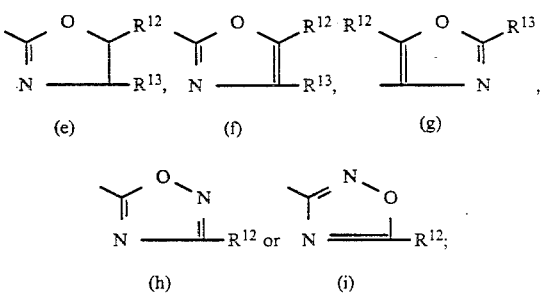

$R^{12}$ and $R^{13}$ each independently are hydrogen, $C_{1-4}$alkyl, aryl or aryl$C_{1-4}$alkyl;
wherein each aryl is phenyl, optionally substituted with 1 or 2 substituents each independently selected from halo, $C_{1-4}$alkyl, trifluoromethyl, $C_{1-4}$alkyloxy or hydroxy.

As used in the foregoing definitions the term "halo" is generic to fluoro, chloro, bromo and iodo; the term "$C_{1-4}$alkyl" defines straight and branch chained saturated hydrocarbon radicals, having from 1 to 4 carbon atoms such as, for example, methyl, ethyl, propyl, 1-methylethyl, butyl, 1,1-dimethylethyl and the like; the term "$C_{3-6}$cycloalkyl" defines cyclopropyl, cyclobutyl, cyclopentyl and cyclohexyl; the term "$C_{3-5}$alkenyl" defines straight and branch chained hydrocarbon radicals containing one double bond and having from 3 to 5 carbon atoms such as, for example, 2-propenyl, 3-butenyl, 2-butenyl, 2-pentenyl, 3-pentenyl, 3-methyl-2-butenyl and the like; "$C_{3-5}$alkynyl" defines straight and branch chained hydrocarbon radicals containing one triple bond and having from 3 to 5 carbon atoms such as, propargyl, 2-butynyl, 3-butynyl, 2-pentynyl, 3-pentynyl or 4-pentynyl, and when a $C_{3-5}$alkenyl or $C_{3-5}$alkynyl is substituted on a heteroatom, then the carbon atom of said $C_{3-5}$alkenyl or $C_{3-5}$alkynyl connected to said heteroatom preferably is saturated.

The compounds of formula (I) may contain in their structure a keto-enol tautomeric system and consequently said compounds may be present in their keto form as well as in their enol form. Said tautomeric forms in the compounds of formula (I) are intended to be embraced within the scope of the invention.

The said addition salts as mentioned hereinabove are meant to comprise the therapeutically active, and in particular, pharmaceutically acceptable non-toxic addition salt forms which the compounds of formula (I) are able to form. The acid addition salts can conveniently be obtained by treating the base form with appropriate acids such as, for example, inorganic acids, such as hydrohalic acid, e.g. hydrochloric, hydrobromic and the like, and sulfuric acid, nitric acid, phosphoric acid and the like; or organic acids such as, for example, acetic, hydroxyacetic, propanoic, 2-hydroxypropanoic, 2-oxopropanoic, ethanedioic, propanedioic, butanedioic, (Z)-2-butenedioic, (E)-2-butenedioic, 2-hydroxybutanedioic, 2,3-dihydroxybutanedioic, 2-hydroxy-1,2,3-propanetricarboxylic, methanesulfonic, ethanesulfonic, benzenesulfonic, 4-methylbenzenesulfonic, cyclohexanesulfamic, 2-hydroxybenzoic, 4-amino-2-hydroxybenzoic and the like acids. Conversely the salt form can be converted by treatment with alkali into the free base form. The compounds of formula (I) containing acidic protons may also be converted into their therapeutically active and in particular, pharmaceutically acceptable non-toxic metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. the benzathine, N-methyl-D-glucamine, hydrabamine salts, and salts with amino acids such as, for example, arginine, lysine and the like. The term acid addition salt also comprises the hydrates and solvent addition forms which the compounds of formula (I) are able to form. Examples of such forms are e.g. hydrates, alcoholates and the like.

From formula (I) it is evident that the compounds of this invention have at least one asymmetric carbon atom in their structure, namely the substituted carbon atom located on the 2-position of the (thio)morpholinyl or piperazinyl nucleus. The absolute configuration of this centre may be indicated by the stereochemical descriptors R and S, this R and S notation corresponding to the rules described in Pure Appl. Chem. 1976, 45, 11–30. Unless otherwise mentioned or indicated, the chemical designation of compounds denotes the mixture of all possible stereochemically isomeric forms, said mixtures containing all diastereomers and enantiomers of the basic molecular structure. Stereochemically isomeric forms of the compounds of formula (I) are obviously intended to be embraced within the scope of the invention.

Particular compounds of formula (I) are those compounds within the invention wherein Het is a radical of formula (a) wherein $R^6$ represents hydrogen, $C_{1-4}$alkyl, $C_{1-4}$alkylthio, halo, $C_{1-4}$alkylsulfinyl or $C_{1-4}$alkylsulfonyl, and $R^7$ and $R^8$ are both hydrogen; or a radical of formula (b) wherein $R^9$ represents hydrogen, halo, $C_{1-4}$alkyl, amino or aryl; or a radical of formula (c) wherein $R^{10}$ represents hydrogen, halo or nitro and $R^{11}$ represents hydrogen or $C_{1-4}$alkyloxycarbonyl; or a radical of formula (d) wherein m is 2.

Other particular compounds are those compounds within the invention wherein $R^1$ and $R^2$ each independently are hydrogen or halo; and/or $R^3$ is a radical of formula —$COOR^4$ wherein $R^4$ represents $C_{1-4}$alkyl, $C_{3-5}$alkenyl, $C_{3-5}$alkynyl or $C_{1-4}$alkyloxy-$C_{1-4}$alkyl, or $R^3$ is a heterocycle of formula (e), (f), (g), (h) or (i) wherein $R^{12}$ and $R^{13}$ each independently represent hydrogen or $C_{1-4}$alkyl, said $R^3$ being preferably located on the 4-position.

Among the above subgroups those compounds of formula (I) are preferred wherein Het is a radical of formula (a) wherein $R^6$ represents $C_{1-4}$alkyl, halo or $C_{1-4}$alkylthio, or a radical of formula (b) wherein $R^9$ represents $C_{1-4}$alkyl or halo; and/or $R^1$ and $R^2$ are both hydrogen; and/or $R^3$ is $C_{1-4}$alkyloxycarbonyl or a 1,2,4-oxadiazol-5-yl of formula (h) with $R^{12}$ being $C_{1-4}$alkyl; and/or n is 1, 2 or 3.

More preferred compounds of formula (I) are those preferred compounds wherein Het is a radical of formula (a) wherein $R^6$ represents methyl, chloro, bromo, iodo or methylthio, or a radical of formula (b) wherein $R^9$ represents methyl, chloro, bromo or iodo; and/or n is 1 or 2.

Particularly preferred compounds within the invention are those more preferred compounds wherein Het is a radical of formula (a) wherein $R^6$ represents iodo, bromo or methylthio; or a radical of formula (b) wherein $R^9$ represents methyl or bromo; n is 2; and $R^3$ is methoxycarbonyl, ethoxycarbonyl or 3-ethyl-1,2,4-oxadiazol-5-yl.

The most preferred compounds within the invention are selected from ethyl 4-[2-[4-(6-iodo-3-pyridazinyl)-2-morpholinyl]ethoxy]benzoate, ethyl 4-[2-[4-[6-(methylthio)-3-pyridazinyl]-2-morpholinyl]ethoxy]benzoate, the stereochemically isomeric forms and the pharmaceutically acceptable addition salts thereof.

The compounds of formula (I) can generally be prepared by reacting an amine of formula (II) with a heterocycle of formula (III) following art-known N-alkylation procedures.

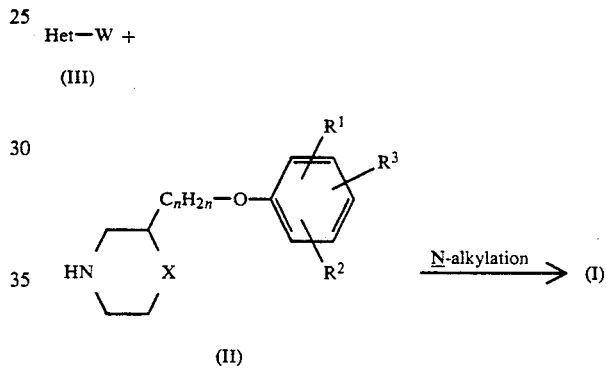

In the foregoing and following reaction schemes W represents an appropriate reactive leaving group such as, for example, halo, e.g. fluoro, chloro, bromo, iodo, or in some instances W may also be a sulfonyloxy group, e.g. 4-methylbenzensulfonyloxy, benzenesulfonyloxy, 2-naphthalenesulfonyloxy, methanesulfonyloxy, trifluoromethanesulfonyloxy and the like reactive leaving groups. The N-alkylation reaction can conveniently be carried out by mixing the reactants, optionally in a reaction-inert solvent such as, for example, water; an aromatic solvent, e.g. benzene, methylbenzene, dimethylbenzene, chlorobenzene, methoxybenzene and the like; a $C_{1-6}$alkanol, e.g. methanol, ethanol, 1-butanol and the like; a ketone, e.g. 2-propanone, 2-butanone, 4-methyl-2-pentanone and the like; an ester, e.g. ethyl acetate, γ-butyrolactone and the like; an ether, e.g. 1,1'-oxybisethane, tetrahydrofuran, 1,4-dioxane and the like; a dipolar aprotic solvent, e.g. N,N-dimethylformamide, N,N-dimethylacetamide, dimethylsulfoxide, pyridine, 1,3-dimethyl-3,4,5,6-tetrahydro-2(1H)-pyrimidinone, 1,3-dimethyl-2-imidazolidinone, 1,1,3,3-tetramethylurea, 1-methyl-2-pyrrolidinone, nitrobenzene, acetonitrile and the like; or a mixture of such solvents. The addition of an appropriate base such as, for example, an alkali metal or an earth alkaline metal carbonate, hydrogen carbonate, hydroxide, oxide, carboxylate, alkoxide, hydride or amide, e.g. sodium carbonate, sodium hydrogen carbonate, potassium carbonate, sodium hydroxide, calcium oxide, sodium acetate, sodium methoxide, sodium hydride, sodium amide and the like, or an organic base such as, for example, a tertiary amine, e.g. N,N-diethylethanamine, N-(1-methylethyl)-2-propanamine, 4-ethylmorpholine, 1,4-diazabicyclo[2.2.2]octane, pyridine and the like, may optionally be used to pick up the acid which is formed during the course of the reaction. In some instances the addition of a iodide salt, preferably an alkali metal iodide, or a crown ether, e.g. 1,4,7,10,13,16-hexaoxacyclooctadecane and the like, may be appropriate. Stirring and somewhat elevated temperatures may enhance the rate of the reaction; more in particular the reaction may be conducted at the reflux temperature of the reaction mixture. Additionally, it may be advantageous to conduct said N-alkylation reaction under an inert atmosphere such as, for example, oxygen-free argon or nitrogen gas.

Alternatively, said N-alkylation reaction may be carried out by applying art-known conditions of phase transfer catalysis reactions. Said conditions comprise stirring the reactants, with an appropriate base and optionally under an inert atmosphere as defined hereinabove, in the presence of a suitable phase transfer catalyst such as, for example, a trialkyphenylmethylammonium, tetraalkylammonium, tetraalkylphosphonium, tetraarylphosphonium halide, hydroxide, hydrogen sulfate and the like catalysts. Somewhat elevated temperatures may be appropriate to enhance the rate of the reaction.

In this and the following preparations, the reaction products may be isolated from the reaction mixture and, if necessary, further purified according to methodologies generally known in the art such as, for example, extraction, distillation, crystallization, trituration and chromatography.

The compounds of formula (I) can also be prepared by alkylating a phenol of formula (V) with an intermediate of formula (IV).

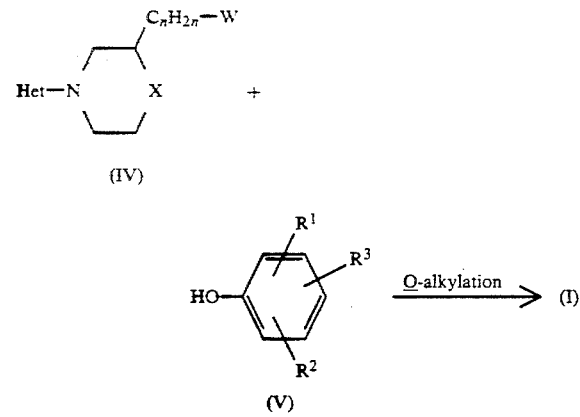

Said O-alkylation reaction can conveniently be carried out by mixing the reactants, optionally in a reaction-inert solvent such as, for example, water; an aromatic solvent, e.g. benzene, methylbenzene, dimethylbenzene and the like; a $C_{1-6}$alkanol, e.g. methanol, ethanol and the like; a ketone, e.g. 2-propanone, 4-methyl-2-pentanone and the like; an ester, e.g. ethyl acetate, γ-butyrolactone and the like; an ether, e.g. 1,1'-oxybisethane, tetrahydrofuran, 1,4-dioxane and the like; a dipolar aprotic solvent, e.g. N,N-dimethylformamide, N,N-dimethylacetamide, dimethylsulfoxide and the like; or a mixture of such solvents. The addition of an appropriate base such as, for example, an alkali metal or an earth alkaline metal carbonate, hydrogen carbonate, hydroxide, oxide, carboxylate, alkoxide, hydride or amide, e.g. sodium carbonate, sodium hydrogen carbonate, potassium carbonate, sodium hydroxide, calcium oxide, sodium acetate, sodium methoxide, sodium hydride, sodium amide and the like, or an organic base such as, for example, a tertiary amine, e.g. N,N-diethylethanamine, N-(1-methylethyl)-2-propanamine and the like, may optionally be used to pick up the acid which is formed during the course of the reaction. Further, it may be advantageous to convert the intermediate of formula (V) first into a suitable salt form thereof such as, for example, an alkali or earth alkaline metal salt, by reacting (V) with an appropriate base as defined hereinabove and subsequently using said salt form in the reaction with the alkylating reagent of formula (IV). Stirring and somewhat elevated temperatures may enhance the rate of the reaction; more in particular the reaction may be conducted at the reflux temperature of the reaction mixture. Additionally, it may be advantageous to conduct said alkylation reaction under an inert atmosphere such as, for example, oxygen-free argon or nitrogen gas.

Alternatively, said O-alkylation reaction may be carried out by applying art-known conditions of phase transfer catalysis reactions as described hereinbefore.

The compounds of formula (I) can alternatively be prepared by reacting a phenol of formula (V) with an alcohol of formula (VI) in the presence of a mixture of diethyl azodicarboxylate and triphenylphosphine.

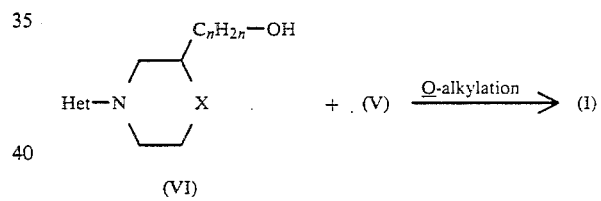

The reaction of (VI) with (V) can conveniently be conducted in an anhydrous reaction-inert solvent preferably under mild neutral conditions at room temperature or below. A suitable reaction-inert solvent is, for example, an aliphatic hydrocarbon, e.g. hexane and the like; an ether, e.g. 1,1'-oxybisethane, 2,2'-oxybispropane, tetrahydrofuran, 1,4-dioxane and the like; a dipolar solvent, e.g. hexamethylphosphoric triamide, N,N-dimethylformamide and the like; or a mixture of such solvents.

The compounds of formula (I) may also be prepared by reacting an alcohol of formula (VI) with an appropriate reagent of formula (VII) according to the hereinbefore described O-alkylation procedures for the preparation of (I) from (IV) and (V).

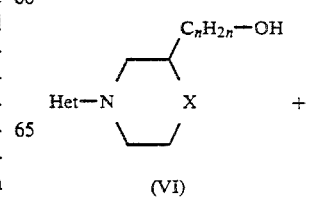

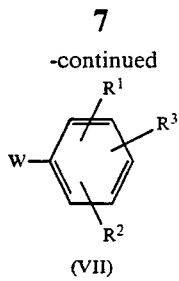

(VII)

The compounds of formula (I), wherein X represents $NR^5$ or S, said compounds being represented respectively by formula (I-1) and (I-2), can be prepared by converting the two alcohol functions of intermediate (VIII) into appropriate leaving groups with appropriate halogenating agents such as, for example, thionyl chloride, sulfuryl chloride, pentachlorophosphorane, pentabromophosphorane or with an appropriate sulfonyl halide, such as, for example, methanesulfonyl chloride or 4-methylbenzenesulfonyl chloride to obtain intermediates of formula (IX). The reaction can be carried out in aromatic hydrocarbons such as methylbenzene, ethylbenzene and the like; dipolar aprotic solvents such as, N,N-dimethylformamide, N,N-dimethylacetamide and the like or a mixture of such solvents. Subsequently the piperazinyl of (I-1) or the thiomorpholinyl moiety of (I-2) can be obtained by cyclizing (IX) respectively in the presence of an amine ($NH_2R^5$) or in the presence of sodium sulfide and sulfur powder.

Compounds of formula (I) wherein $R^3$ is a substituted or unsubstituted 4,5-dihydro-2-oxazolyl of formula (e), said compounds being represented by (I-e), can be prepared following procedures described in EP-A-207,454 and EP-A-137,242. For example an appropriate acid, acyl halide or alkyl ester can be condensed with a substituted or unsubstituted hydroxyalkylamine to give a hydroxyalkylamide. The latter may in situ or, if desired, after isolating and purifying it, be cyclized by stirring with thionyl chloride or phosphorous trichloride optionally in the presence of a suitable inert solvent such as, an ether, e.g. tetrahydrofuran, 1,4-dioxane and the like, a halogenated hydrocarbon, e.g. trichloromethane, dichloromethane, an ester, e.g. ethyl acetate, isopropyl acetate and the like solvents.

The compounds of formula (I) wherein $R^3$ is a 1,2,4-oxadiazol-5-yl-ring of formula (h), said compounds being represented by formula (I-h), can be prepared by reacting a compound of formula (X), wherein $R^{14}$ is hydrogen or $C_{1-4}$alkyl, with an amidoxime of formula (XI).

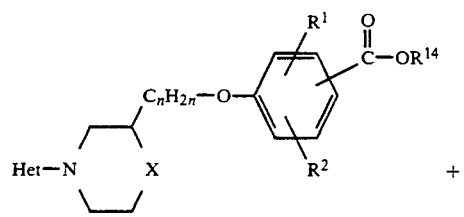

+

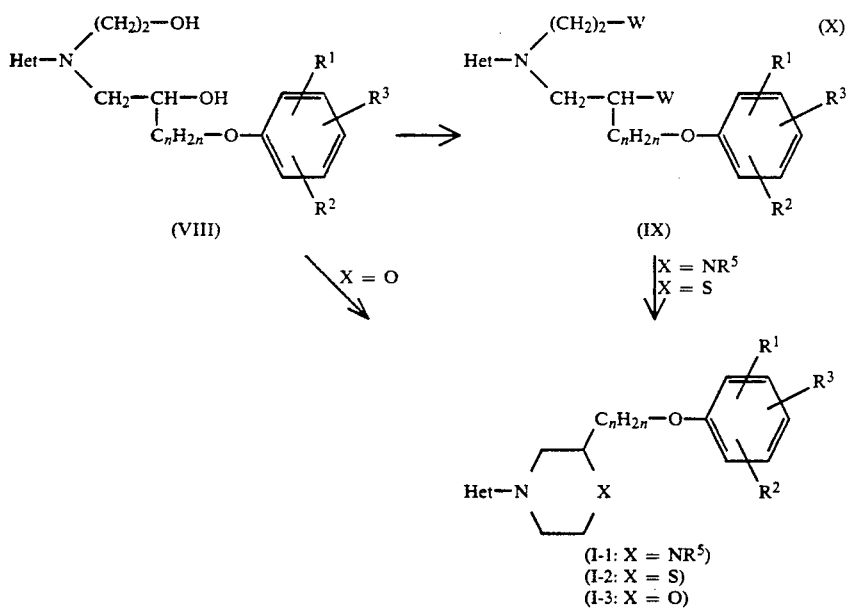

(I-1: X = $NR^5$)
(I-2: X = S)
(I-3: X = O)

The compounds of formula (I), wherein X represents O, said compounds being represented by formula (I-3) can be prepared by cyclizing (VIII) in the presence of a dehydrating agent such as, for example, a mixture of diethyl azodicarboxylate and triphenylphosphine. The reaction can be conducted in a reaction-inert solvent such as, for example, a hydrocarbon, e.g. hexane, dichloromethane, trichloromethane, and the like; an ether, e.g. 1,1'-oxybisethane, tetrahydrofuran and the like.

The compounds of formula (I) can also be converted into each other following art-known functional group transformation procedures.

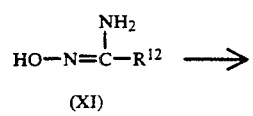

(XI)

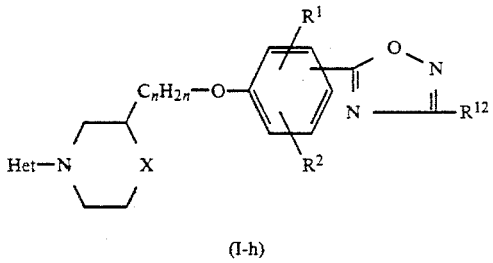

(I-h)

The compounds of formula (I) wherein $R^3$ is a 1,2,4-oxadiazol-3-yl ring of formula (i), said compounds being represented by formula (I-i), can be prepared by reacting a compound of formula (I) wherein $R^3$ is cyano, represented by formula (I-j), with hydroxylamine or an acid addition salt thereof and reacting the thus formed amidoxime with a carboxylic acid of formula (XII) or a reactive functional derivative thereof such as, for example, a halide, an anhydride or an ortho ester form thereof.

sponding acyl halides by treatment with a suitable halogenating agent such as, for example, thionyl chloride, pentachlorophosphorane and sulfuryl chloride. Said acyl halides and said acids can further be derivatized to the corresponding esters by reacting said acids or acyl halides with a suitable alkanol following art-known esterification reaction procedures. Said reactions are most conveniently conducted in an appropriate solvent such as, for example, tetrahydrofuran, dichloromethane, trichloromethane, acetonitrile and the like solvents.

The compounds of formula (I) wherein the radical $R^3$ is an ester group may be converted into the corresponding carboxylic acid following art-known saponification procedures, e.g. by treating the starting compound with an aqueous alkaline or an aqueous acidic solution.

The compounds of formula (I), wherein Het is a radical of formula (a) with $R^6$ being halo, may be converted into compounds of formula (I) wherein $R^6$ is hydrogen following art-known hydrogenolysis procedures, i.e. by stirring and, if desired, heating the starting compounds in a suitable reaction-inert solvent, such as an alkanol,

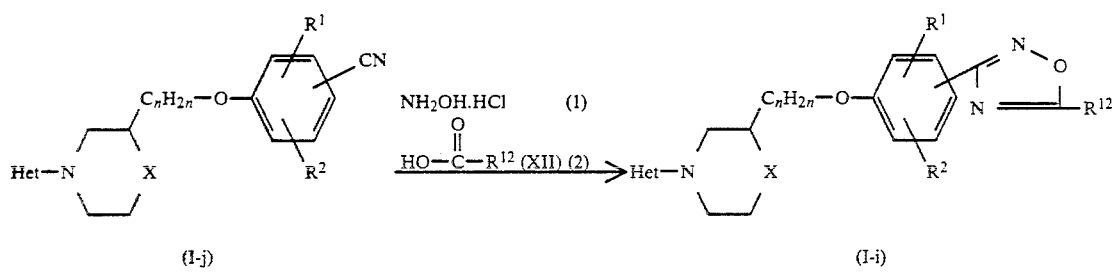

The condensation reactions to prepare compounds (I-h) and (I-i) can be carried out by stirring and if desired heating the starting materials, neat or in a suitable reaction-inert solvent and optionally in the presence of an appropriate base such as, for example, an alkoxide, hydride or amide, e.g. sodium methoxide, sodium ethoxide, sodium hydride, sodium amide and the like. Suitable solvents for said condensation reactions are for example, ethers, e.g. 1,1'-oxybisethane, tetrahydrofuran, 1,4-dioxane, 1,2-dimethoxyethane and the like; alkanols, e.g. methanol, ethanol, propanol, butanol and the like; or mixtures of such solvents. The water, acid or hydrohalic acid which is liberated during the condensation may be removed from the reaction mixture by azeotropical destillation, complexation, salt formation and the like methods.

The compounds wherein $R^3$ is cyano may be hydrolysed thus yielding compounds of formula (I) wherein the radical $R^3$ is a carboxyl group. Said hydrolysis reaction is preferably conducted in an aqueous acidic medium, e.g. in aqueous sulfuric, hydrochloric or phosphoric acid solution, at room temperature or at a slightly increased temperature. It may be advantageous to add a second acid to the reaction mixture, e.g. acetic acid.

The compounds of formula (I) wherein the radical $R^3$ is a carboxyl group may be converted into the corree.g. methanol or ethanol, in the presence of hydrogen and an appropriate catalyst such as, for example, palladium-on-charcoal and the like catalysts. Said halo atoms may be replaced by a $C_{1-4}$alkyloxy or $C_{1-4}$alkylthio substituent by reacting the starting compound with an appropriate alcohol or thioalcohol or preferably an alkali metal or earth alkaline metal salt of said alcohol or thioalcohol, optionally in the presence of an appropriate catalyst such as, for example, a copper salt.

A number of intermediates and starting materials in the foregoing preparations are known compounds which may be prepared according to art-known methodologies of preparing said or similar compounds and some intermediates are new. A number of such preparation methods will be described hereinafter in more detail.

In the next reaction scheme there are mentioned some different ways of preparing intermediates of formula (XV), which can be converted into intermediates of formula (II) by removing the protective group P. The symbol P represents a suitable protective group which is readily removable by hydrogenation or hydrolysis. Preferred protective groups are, for example, hydrogenolyzable groups, e.g. phenylmethyl, phenylmethoxycarbonyl and the like, or hydrolyzable groups, e.g. $C_{1-4}$alkylcarbonyl, $C_{1-4}$alkylphenylsulfonyl and the like.

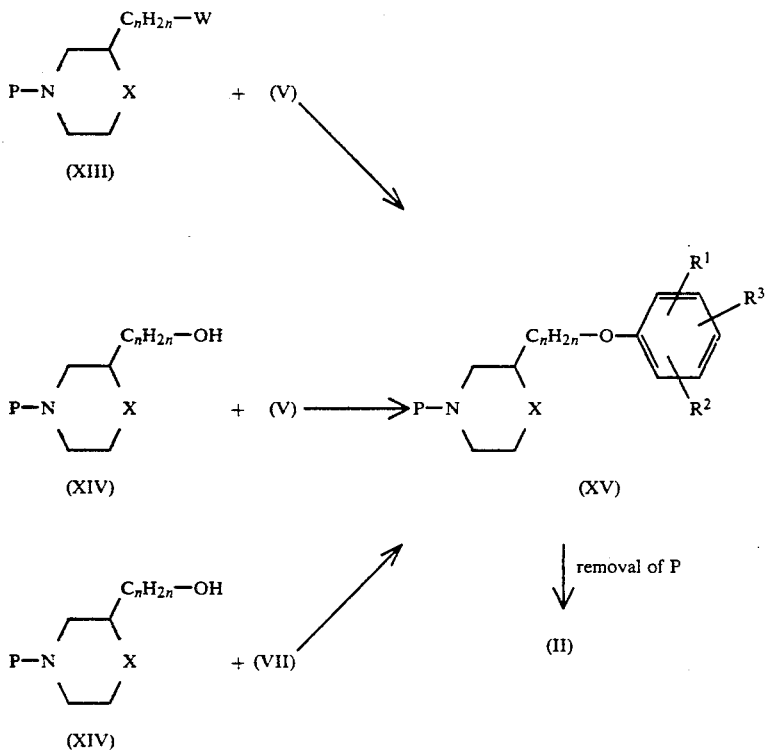

The intermediates of formula (XV) can be prepared by O-alkylating an alcohol of formula (V) with a reagent of formula (XIII), or by reacting a phenol of formula (V) with an alcohol of formula (XIV) or alternatively by reacting the alcohol (XIV) with an appropriate reagent of formula (VII). All these procedures are described hereinbefore for the preparation of compound (I).

The intermediates of formula (II) wherein $R^3$ is a heterocycle of formula (e), (f), (h) or (i), can also be prepared by cyclizing an appropriate (thio)morpholinyl or piperazinyl alkylphenol ether (XVI). For example, the intermediates of formula (II) wherein $R^3$ is a 1,2,4-oxadiazol-5-yl ring of formula (h), said intermediates being represented by formula (II-h), can also be prepared by reacting an intermediate of formula (XVI-h) with an amidoxime of formula (XI) as described hereinbefore for the preparation of (I-h) from (X) and (XI).

-continued

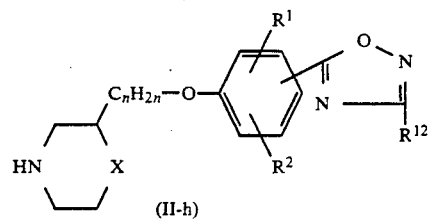

The intermediates of formula (II) wherein $R^3$ is a 1,2,4-oxadiazol-3-yl ring of formula (i), said intermediates being represented by formula (II-i), can be obtained by reacting an intermediate of formula (XVI-i) with hydroxylamine or an acid addition salt thereof and reacting the thus formed intermediate with a carboxylic acid of formula (XII) or a functional derivative thereof, such as, for example, a halide, an anhydride or an ortho ester form thereof. The reaction can be carried out following the same procedure as described for the synthesis of (I-i) from (I-j) and (XII).

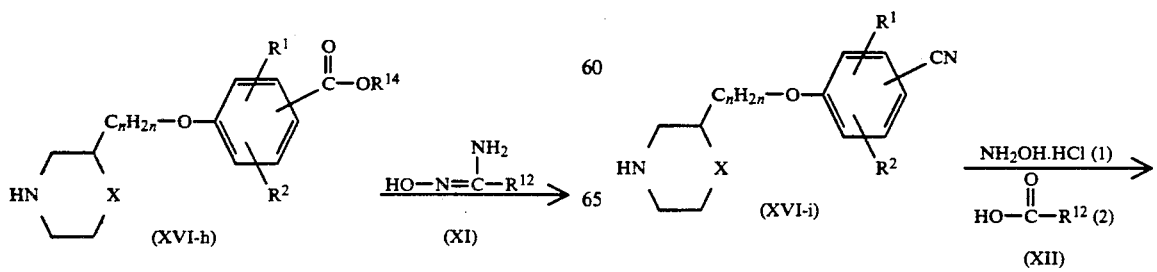

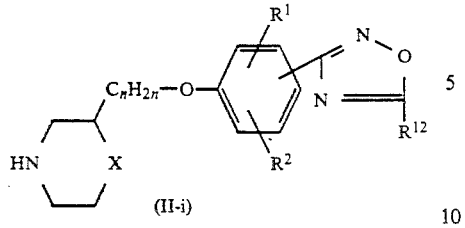

(II-i)

Intermediates of formula (II), wherein X is NR⁵, said intermediates being represented by formula (II-1-a) (R⁵ is hydrogen) and (II-1-b) (R⁵ is other than hydrogen) can be prepared according the following reaction scheme. Intermediate (XVII) can be obtained by reacting a 2-pyrazinealcohol with a phenol derivative following reaction procedures described hereinbefore. The 2-pyrazinyl derivative of formula (XVII) can then be reduced with hydrogen in the presence of an appropriate catalyst such as, for example, platinum-on-charcoal, palladium-on-charcoal, Raney nickel and the like, in a suitable reaction-inert solvent like methanol or ethanol to yield a 2-piperazinyl derivative of formula (II-1-a).

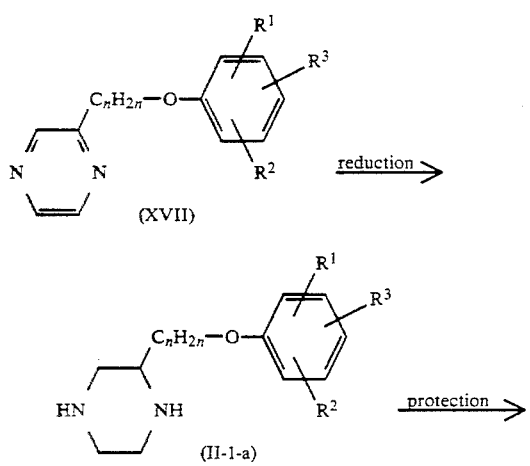

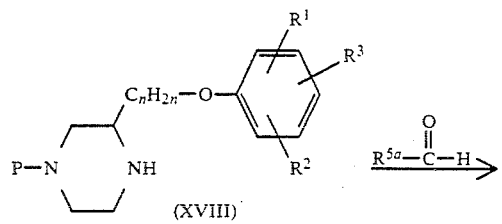

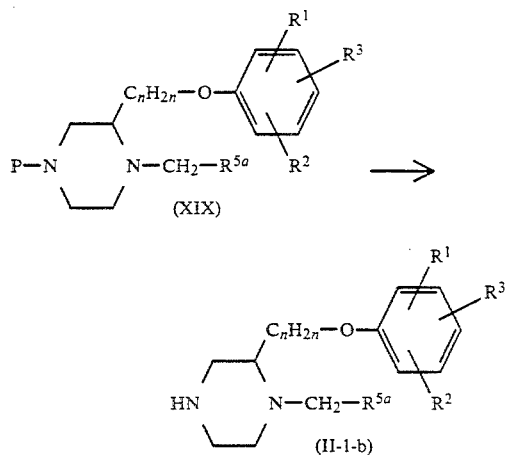

To alkylate only the N-1-position of the 2-piperazinyl derivative of formula (II-1-a), it is necessary to protect the N-4-position with, for example, a phenylmethyl group, an (aryl or $C_{1-4}$alkyl)oxycarbonyl group and the like. The thus obtained intermediate of formula (XVIII) can be reductively N-alkylated with a reagent of formula $R^{5a}$—CHO, wherein $R^{5a}$ represents hydrogen, $C_{1-3}$alkyl, aryl or aryl$C_{1-3}$alkyl, in a reaction-inert solvent in the presence of hydrogen and a suitable catalyst. Said intermediate of formula (XIX) can be converted into an intermediate of formula (II-1-b) by removing the protective group following art-known procedures.

Intermediates of formula (II) can also be obtained as described in the following reaction scheme.

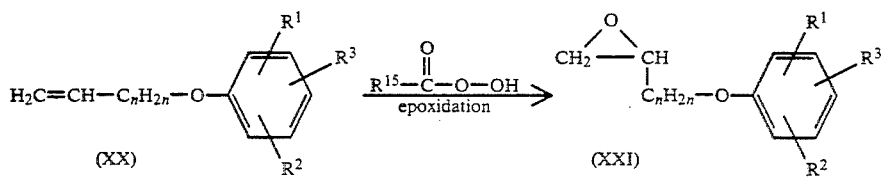

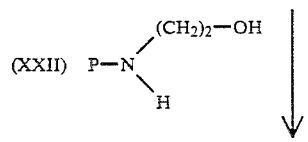

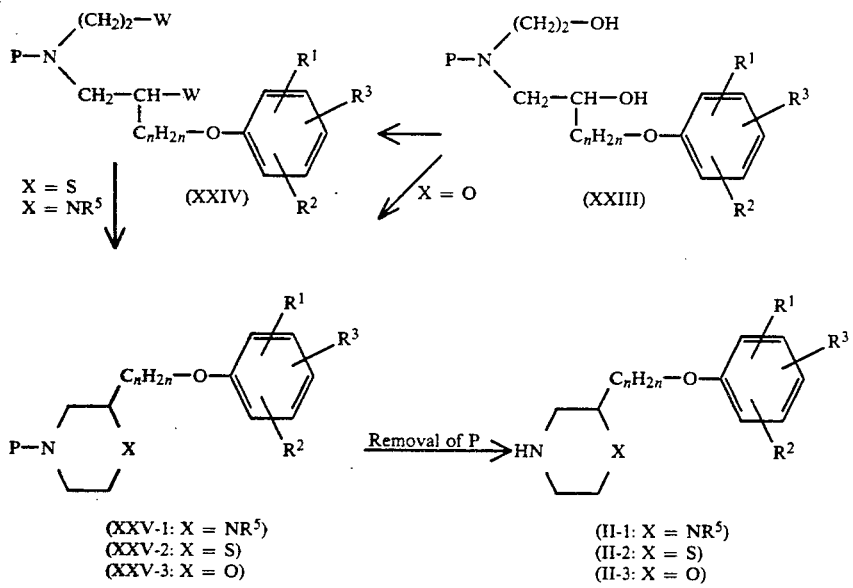

The alkene moiety of intermediate (XX), prepared by reacting a phenol derivative with an alkenylhalide, can be epoxidized with a peroxycarboxylic acid of formula $R^{15}$—COOOH to give an oxacyclopropane. $R^{15}$ is an optionally substituted aryl ring. Said oxidation reaction can be carried out in a suitable reaction-inert solvent such as a halogenated hydrocarbon, e.g. dichloromethane, trichloromethane, 1,2-dichloroethane and the like. Reaction of the oxacyclopropane moiety of formula (XXI) with an amine of formula (XXII) gives an alcohol intermediate of formula (XXIII). The reaction can be carried out in alcohols, e.g. methanol, ethanol, 2-propanol and the like solvents, optionally at reflux temperature of the solvent. The intermediates of formula (XXV), wherein X represents $NR^5$ or S, said intermediates being represented by respectively formula (XXV-1) or (XXV-2) can be prepared by converting the two alcohol functions of (XXIII) into appropriate leaving groups. Subsequently, the intermediates (XXIV) can be cyclized in the presence of an amine or in the presence of sodium sulfide and sulfur powder to yield respectively intermediates (XXV-1) and (XXV-2), as described hereinbefore for the preparation of (I-1) and (I-2) from (VIII). The intermediates of formula (XXV), wherein X represents O, said intermediates being represented by formula (XXV-3), can be prepared by cyclizing (XXIII) in the presence of a dehydrating agent, as described for the preparation of (I-3) from (VIII). The intermediates of formula (II-1), (II-2) and (II-3) can be obtained by removing the protective group P by hydrogenation or hydrolysis depending on the nature of P.

Intermediates of formula (VIII) can be prepared by removing the protective group P in formula (XXIII) by hydrogenation or hydrolyses and subsequently N-alkylating the thus obtained amine of formula (XXVII) with a heterocycle of formula (III) as described for the preparation of (I) from (II) and (III).

(XXIII) ⟶

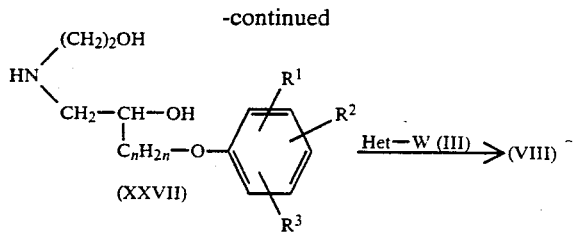

Intermediates of formula (IV) can be prepared by N-alkylating a heterocycle of formula (III) with an amine of formula (XXVIII) following art-known N-alkylation procedures described hereinbefore for the preparation of (I) from (II) and (III), and subsequently converting the alcohol function of the thus obtained intermediate (VI) into an appropriate leaving group as described for the preparation of (XXIV) from (XXIII).

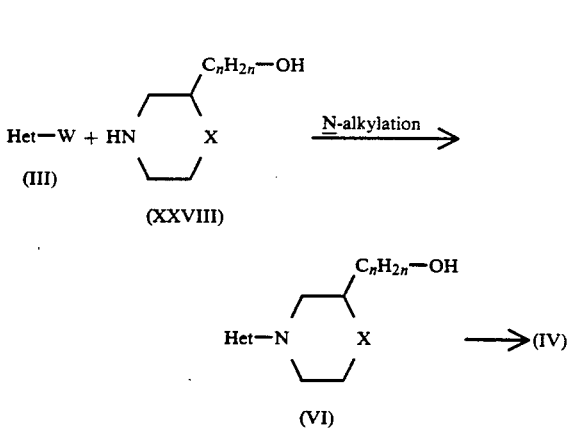

Intermediates of formula (XIV) can be prepared by reducing the carbonyl group of intermediate (XXIX), wherein $R^{17}$ is hydrogen, $C_{1-4}$alkyloxy or hydroxy, with a reducing agent such as, for example, lithium aluminum hydride or sodium borohydride in a suitable reaction-inert solvent, e.g. tetrahydrofuran and the like. The alcohol function can be converted into an appropriate leaving group as described hereinabove, thus yielding an intermediate of formula (XIII).

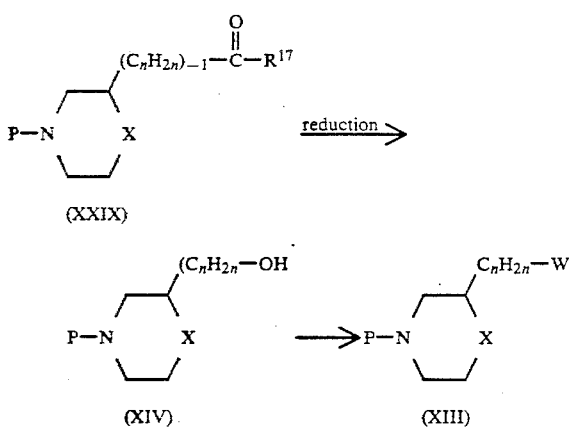

Starting materials and intermediates used in all of the preceding procedures for which no specific preparation is given herein, may be prepared according to similar procedures as described hereinbefore for compounds of formula (I), and/or may be prepared following art-known methodologies described in the literature for the preparation of similar known compounds.

The compounds of formula (I) and some of the intermediates in this invention have at least one asymmetric carbon atom in their structure namely the substituted carbon atom located on the 2-position of the (thio)morpholinyl or piperazinyl nucleus. Pure stereochemically isomeric forms of said compounds and said intermediates can be obtained by the application of art-known procedures. For example, diastereoisomers can be separated by physical methods such as selective crystallization or chromatographic techniques, e.g. counter current distribution, liquid chromatography and the like methods. Enantiomers can be obtained from racemic mixtures by first converting said racemic mixtures with suitable resolving agents such as, for example, chiral acids, to mixtures of diastereomeric salts or compounds; then physically separating said mixtures of diastereomeric salts or compounds by, for example, selective crystallization or chromatographic techniques, e.g. liquid chromatography and the like methods; and finally converting said separated diastereomeric salts or compounds into the corresponding enantiomers. Alternatively, enantiomerically pure compounds and intermediates may also be obtained by chromatography of the racemate over a chiral stationary phase and the like techniques. Pure stereochemically isomeric forms of the compounds of formula (I) may also be obtained from the pure stereochemically forms of the appropriate intermediates and starting materials, provided that the intervening reactions occur stereospecifically.

The compounds of formula (I) and the pharmaceutically acceptable addition salts and stereoisomeric forms show antiviral activity and are attractive due to their favourable therapeutic index, resulting from an acceptable low degree of cell toxicity, combined with satisfactory antiviral activity.

The antiviral properties of the compounds of formula (I) can be demonstrated for example in the "Picornavirus Minimal Inhibitory Concentration (MIC)"-test, illustrating the useful antiviral activity of the compounds of the present invention.

The compounds of the present invention are therefore useful agents for inhibiting the growth and/or replication of viruses. The compounds of formula (I), the pharmaceutically acceptable addition salts and stereochemically isomeric forms thereof are active against a broad spectrum of picornaviruses, including enteroviruses e.g. Coxsackieviruses, Echoviruses, Enteroviruses, e.g. Enterovirus 70 and especially numerous strains of rhinoviruses, e.g. Human Rhinovirus serotypes HRV -2,-3,-4,-5,-6,-9,-14,-15,-29,-39,-42,-45,-51,-59,-63,-70,-72-,-85,-86 and the like. Quite unexpectedly the compounds of formula (I) also show anti-rhinoviral activity on Human Rhinovirus serotypes HRV 41 and 89.

In view of their potent, local as well as systemic, antiviral activity the compounds of this invention constitute useful tools for inhibiting, combating or preventing the growth of viruses. More particularly there is provided a method of treating viral diseases in warm-blooded animals suffering from said viral diseases, especially respiratory diseases e.g. common cold, pneumonia, bronchiolitis, herpangina and the like, CNS-diseases e.g. paralysis, aseptic meningitis, encephalitis and the like, cardiac disease e.g. pericarditis, myocarditis and the like, hepatic diseases e.g. hepatitis and the like, gastrointestinal diseases e.g. diarrhea and the like, ophtalmic diseases e.g. acute hemorrhagic conjunctivitis and the like, dermatological diseases e.g. exanthem, rash, hand-foot-and-mouth disease, and the like diseases. Said method comprises the systemic or topical administration to warm-blooded animals of an antivirally effective amount of a compound of formula (I), a pharmaceutically acceptable addition salt or a stereoisomeric form thereof. Some compounds of the invention are especially useful to treat respiratory diseases, like common cold due to their prolonged in vivo activity in the buccal and nasal cavity.

The subject compounds may be formulated into various pharmaceutical forms for systemic or topical administration purposes. To prepare the pharmaceutical compositions of this invention, an effective amount of the particular compound, optionally in acid-addition salt form, as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, particularly, for administration orally, rectally, percutaneously, intranasally, by parenteral injection or for ophtalimic administration. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules, and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. Also included are solid form preparations which are intended to be converted, shortly before use, to liquid form preparations. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. Said additives may facilitate the administration to the skin and/or may be helpful for preparing the desired compositions. These compositions can take the form of creams, lotions, aerosols and/or emulsions and can be included in a transdermal patch of the matrix or reservoir type as are conventional in the art for this purpose. In the compositions suitable for topical administration the active ingredient will preferably be a semisolid such as a thickened composition such as salves, creams, gellies, ointments and the like which can be applied by a swab. Pharmaceutical composition suitable for topical administration may also be in form of drops, lotions or an aerosol. Suitable aerosol preparations may include solutions and solids in powder form, which may be in combination with a pharmaceutically acceptable carrier, such as an inert compressed gas. Acid addition salts of (I) due to their increased water solubility over the corresponding base form, are obviously more suitable in the preparation of aqueous compositions.

In a further aspect of the invention there are provided particular pharmaceutical compositions which comprise a compound of formula (I), a pharmaceutically acceptable addition salt or a stereochemically isomeric form thereof and a cyclodextrin or a derivative thereof. When applied to the site of infection such cyclodextrin based compositions result in a continuous and controlled delivery of sufficiently high concentrations of the antiviral compound of formula (I) to the site of the infection for sustained periods of time.

Such compositions are particularly convenient for treating local viral infections, in particular mucosal infections, e.g. nasal or eye infections.

The cyclodextrin to be used in the aforementioned compositions include the pharmaceutically acceptable unsubstituted and substituted cyclodextrins known in the art, more particularly $\alpha$, $\beta$ or $\gamma$ cyclodextrins or the pharmaceutically acceptable derivatives thereof.

Substituted cyclodextrins which can be used in the invention include polyethers described in U.S. Pat. No. 3,459,731 which is incorporated by reference for the definition and processes for preparation. In general, unsubstituted cyclodextrins are reacted with an alkylene oxide, preferably under superatmospheric pressure and at an elevated temperature, in the presence of an alkaline catayst. Since a hydroxy moiety of the cyclodextrin can be substituted by an alkylene oxide which itself can react with yet another molecule of alkylene oxide, the average molar substitution (MS) is used as a measure of the average number of moles of the substituting agent per glucose unit. The MS can be greater than 3 and theoretically has no limit.

Further substituted cyclodextrins are ethers wherein the hydrogen of one or more cyclodextrin hydroxy groups is replaced by $C_{1-6}$alkyl, hydroxyl$C_{1-6}$alkyl, carboxy$C_{1-6}$alkyl or $C_{1-6}$alkyloxycarbonyl$C_{1-6}$alkyl or mixed ethers thereof. In particular such substituted cyclodextrins are ethers wherein the hydrogen of one or more cyclodextrin hydroxy groups is replaced by $C_{1-3}$alkyl, hydroxy$C_{2-4}$alkyl or carboxy$C_{1-2}$alkyl or more in particular by methyl, ethyl, hydroxyethyl, hydroxypropyl, hydroxybutyl, carboxymethyl or carboxyethyl. In the foregoing definitions the term "$C_{1-6}$alkyl" is meant to include straight and branched saturated hydrocarbon radicals, having from 1 to 6 carbon atoms, such as, methyl, ethyl, 1-methylethyl, 1,1-dimethylethyl, propyl, 2-methylpropyl, butyl, pentyl, hexyl and the like.

Such ethers can be prepared by reacting the starting cyclodextrin with an appropriate O-alkylating agent or a mixture of such agents in a concentration being selected so that the desired cyclodextrin ether is obtained. The said reaction is preferably conducted in a suitable solvent in the presence of an appropriate base. With such ethers, the degree of substitution (DS) is the average number of substituted hydroxy functions per glucose unit, the DS being thus 3 or less. In the cyclodextrin derivatives for use in the compositions according to the present invention, the DS preferably is in the range of 0.125 to 3, in particular 0.3 to 2, more in particular 0.3 to 1 and the MS is in the range of 0.125 to 10, in particular of 0.3 to 3 and more in particular 0.3 to 1.5.

Other references describing cyclodextrins for use in the compositions according to the present invention, and which provide a guide for the preparation and characteristics of cyclodextrins, for the process of depositing the selected agent within the cavity of the cyclodextrin molecule and for the use of cyclodextrins in pharmaceutical compositions include the following: "Cyclodextrin Technology" by József Szejtli, Kluwer Academic Publishers (1988) in the chapter Cyclodextrins in Pharmaceuticals; "Cyclodextrin Chemistry" by M. L. Bender et al., Springer-Verlag, Berlin (1978); "Advances in Carbohydrate Chemistry", Vol. 12 Ed. by M. L. Wolfrom, Academic Press, New York (157) in the chapter The Schardinger Dextrins by Dexter French at p. 189–260; "Cyclodextrins and their Inclusions Complexes" by J. Szejtli, Akademiai Kiado, Budapest, Hungary (1982); I. Tabushi in Acc. Chem. Research, 1982, 15, p. 66–72; W. Sanger, Angewandte Chemie, 92, p. 343–361 (1981); A. P. Croft and R. A. Bartsch in Tetrahedron, 39, p. 1417–1474 (1983); German Offenlegungsschrift DE 3118218; German Offenlegungsschrift DE 3317064; EP-A-94,157; EP-A-149,197; U.S. Pat. Nos. 4,659,696; and 4,383,992.

Of particular utility in the invention are the $\beta$-cyclodextrin ethers, e.g. dimethyl-$\beta$-cyclodextrin as described in Drugs of the Future, Vol. 9, No. 8, p. 577–578 by M. Nogradi (1984) and polyethers, e.g. hydroxypropyl $\beta$-cyclodextrin and hydroxyethyl $\beta$-cyclodextrin, being examples. Such an alkyl ether may be a methyl ether with a degree of substitution of about 0.125 to 3, e.g. about 0.3 to 2. Such a hydroxypropyl cyclodextrin may for example be formed from the reaction between $\beta$-cyclodextrin an propylene oxide and may have a MS value of about 0.125 to 10, e.g. about 0.3 to 3.

In said particular cyclodextrin based formulation, the molecules of the antiviral compounds of formula (I) are surrounded, at least in part, by the cyclodextrin, i.e. the agent fits into the cyclodextrin cavity.

To prepare said particular cyclodextrin based pharmaceutical compositions of the invention, the selected antiviral compound (or compounds) of formula (I), the pharmaceutically acceptable addition salt of the stereochemically isomeric form thereof is deposited within the cyclodextrin molecule itself, such process being known in the art for other active agents. In the final compositions, the molar ratio of cyclodextrin:antiviral compound is from about 1:1 to about 5:1, in particular, about 1:1 to about 2:1. Thus, in general, the composition will be prepared by dissolving the cyclodextrin in water and adding the antiviral compound to this solution, preferably under vigorous stirring and preferably at a temperature in the range of 10° C. to 50° C., in particular in range of 15° C. to 30° C., and preferably at room temperature.

In the final compositions, the cyclodextrin will comprise about 2.5 to 40% by weight, in particular about 2.5 to 25%, more in particular 5 to 25%, or 5 to 20%, for example about 10%, with the remainder being water, preservative, the active ingredient and any excipients.

In particular, the pharmaceutical compositions may consist only of water, cyclodextrin and the antiviral agents without the need for co-solvents such as ethanol or surfactants.

Application of the cyclodextrin based compositions of the invention may be by aerosol, e.g. with a propellant such as nitrogen, carbon dioxide, a freon, or without a propellant such as a pump spray, drops, or a semisolid such as a thickened compositions which can be applied by a swab. In particular applications, semisolid compositions such as salves, creams, gellies, ointments and the like will conveniently be used.

For the liquid preparations of said cyclodextrin based compositions, any of the usual pharmaceutical media may be added, such as, for example, glycols, oils, alcohols and the like, however in concentrations below the level of irriation. In order to stabilize the formulations the pH may be increased or decreased or stabilized by adding appropriate acids, bases or buffer systems, e.g. citrate, phosphate buffers. Further additives may comprise substances to make the formulations isotonic, e.g. sodium chloride, mannitol, glucose and the like. It is further recommendable to add a preservative to the formulations such as, for example, a mercury salt or complex salt, e.g. phenyl mercuriacetate, nitrate, chloride or borate, phenylethyl alcohol, ethanol, propylene glycol and the like. Suitable thickeners for obtaining the above-mentioned thickened compositions comprise polyvinyl alcohols, hydroxypropyl methyl celluloses, hydroxyethyl celluloses, methylcelluloses, polyvinyl pyrrolidone, acrylic acid polymers and the like.

Depending on the type of virus which is to be controlled, said cyclodextrin based compositions can be applied in the vagina, nose, mouth, eyes, lungs or within the cheeks so as to control viruses which have not entered the blood stream of the patient, e.g. viruses which are located in mucous membranes of the body. The cyclodextrin based compositions of the invention are particularly useful on those infection sites where the natural defense mechanisms prevent the delivery of antiviral agents during sustained periods due to an effective elimination of the active compound from the site of infection. Such elimination may be due to clearance by ciliary movement of secretion, or by absorption.

As part of the pharmaceutical composition, one may also include the same or a different active antiviral in a different delivery carrier so as to provide a different profile of activity, e.g. a wide range of time during which the composition shows activity or a supplement to bolster a low level at a particular point in the release schedule of the cyclodextrin.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, drops, teaspoonfuls, tablespoonfuls and the like, and segregated multiples thereof.

Those of skill in treating antiviral diseases in warm-blooded animals could easily determine the effective amount from the test results presented hereinafter. In general it is contemplated that an effective amount would be from 0.001 mg/kg to 50 mg/kg body weight, preferably from 0.01 mg/kg to 10 mg/kg body weight.

The following examples are intended to illustrate and not to limit the scope of the present invention in all its aspects. Unless otherwise stated all parts therein are by weight.

EXPERIMENTAL PART

A. Preparation of the Intermediates

EXAMPLE 1 a) A mixture of 11.3 parts of 2-chloromethyl-4-(phenylmethyl)morpholine (described in Synth. Comm. 1980, 10(1), 59-73), 8.3 parts of ethyl 4-hydroxybenzoate, 6.9 parts of potassium carbonate and 141 parts of N,N-dimethylformamide was stirred overnight at 110° C. The reaction mixture was evaporated and water was added to the residue. The product was extracted with dichloromethane and the extract was dried, filtered and evaporated. The residue was converted into the (E)-2-butenedioate salt in 2-propanol, yielding 9.5 parts (40.3%) of ethyl 4-[[4-(phenylmethyl)-2-morpholinyl]-methoxy]benzoate (E)-2-butenedioate(1:1); mp. 174.4° C. (interm. 1).

b) A mixture of 8.5 parts of intermediate 1 and 198 parts of ethanol was hydrogenated at normal pressure and at 50° C. with 2 parts of palladium-on-charcoal catalyst 10%. After the calculated amount of hydrogen was taken up, the catalyst was filtered off and the filtrate was evaporated. The residue was basified with NH4OH (conc.) and the product was extracted with trichloromethane. The extract was dried, filtered and evaporated, yielding 5 parts (100%) of ethyl 4-[(2-morpholinyl)methoxy]benzoate (interm. 2).

c) To a stirred mixture of 3.6 parts of N-hydroxypropanimidamide and 89 parts of tetrahydrofuran were added portionwise 40 parts of a sodium hydride dispersion 50%. After stirring for 1 hour at room temperature, a solution of 5.3 parts of intermediate 2 in a small amount of tetrahydrofuran was added. The reaction mixture was stirred and refluxed overnight. After evaporation, the residue was taken up in water. The precipitated product was filtered off and taken up in a mixture of trichloromethane and methanol. The organic layer was dried, filtered and evaporated, yielding 4.4 parts (76.0%) of 2-[[4-(3-ethyl-1,2,4-oxadiazol-5-yl)phenoxy]-methyl]morpholine as a residue (interm. 3).

EXAMPLE 2 a) To a refluxing mixture of 15 parts of lithium aluminum hydride and 534 parts of tetrahydrofuran was added dropwise a solution of 80 parts of ethyl 4-

(phenylmethyl)-2-morpholineacetate (described in C.A.; 93, 26362g) in 89 parts of tetrahydrofuran under a nitrogen atmosphere. Refluxing was continued overnight. After cooling to 0°–5° C., there were added successively 15.6 parts of water, 14.6 parts of NaOH 20% and 51 parts of water. The whole was stirred for ½ hour and then filtered over diatomaceous earth. The filtrate was evaporated, yielding 68 parts (99.1%) of 4-(phenylmethyl)-2-morpholineethanol (interm. 4).

b) To a mixture of 54 parts of thionyl chloride and 266 parts of dichloromethane was added dropwise a solution of 44 parts of intermediate 4 in 266 parts of dichloromethane at 10°–15° C. After stirring overnight, the reaction mixture was evaporated and the residue was co-evaporated with 87 parts of methylbenzene (2×), yielding 56 parts (100%) of 2-(2-chloroethyl)-4-(phenylmethyl)morpholine (interm. 5).

c) To a heated (60° C.) mixture of 56 parts of intermediate 5 monohydrochloride, 64 parts of sodium carbonate and 522 parts of methylbenzene were added dropwise 42.6 parts of phenylmethyl chloroformate. The whole was refluxed for 2 hours and stirred overnight at 20° C. Water was added and the organic layer was separated, dried, filtered and evaporated. The residue was purified by column chromatography (silica gel; $CH_2Cl_2/CH_3OH$ 99:1). The eluent of the desired fraction was evaporated, yielding 42 parts (74.0%) of (phenylmethyl) 2-(2-chloroethyl)-4-morpholinecarboxylate (interm. 6).

d) A mixture of 42 parts of intermediate 6, 24.9 parts of ethyl 4-hydroxybenzoate, 34.5 parts of potassium carbonate and 327 parts of N,N-dimethylformamide was stirred overnight at 110° C. The reaction mixture was evaporated and water was added to the residue. The product was extracted with methylbenzene and the extract was dried, filtered and evaporated. The residue was purified by column chromatography (silica gel; $CH_2Cl_2/CH_3OH$ 99:1). The eluent of the desired fraction was evaporated, yielding 10.8 parts (17.4%) of (phenylmethyl) 2-[2-[4-(ethoxycarbonyl)phenoxy]ethyl]-4-morpholinecarboxylate (interm. 7).

e) A mixture of 10.8 parts of intermediate 7 and 198 parts of ethanol was hydrogenated at normal pressure and at 50° C. with 2 parts of palladium-on-charcoal catalyst 10%. After the calculated amount of hydrogen was taken up, the catalyst was filtered off and the filtrate was evaporated, yielding 6.5 parts (86.2%) of ethyl 4-[2-(2-morpholinyl)ethoxy]benzoate (interm. 8). 4.2 Parts of intermediate 8 were separated into the pure enantiomeric forms by column chromatography (chiralcel OD; hexane/2-propanol 97:3), yielding 1.5 parts (35.7%) of (−)-ethyl 4-[2-(2-morpholinyl)ethoxy]benzoate (interm. 8a) and 0.5 parts (11.9%) of (+)-ethyl 4-[2-(2-morpholinyl)ethoxy]benzoate (interm. 8b).

EXAMPLE 3 a) To a stirred and cooled ($\leq 5°$ C.) solution of 8.3 parts of 2-pyrazinemethanol, 13.3 parts of ethyl 4-hydroxybenzoate and 20.2 parts of triphenylphosphine in 178 parts of tetrahydrofuran was added dropwise a solution of 13.93 parts of diethyl azodicarboxylate in 45 parts of tetrahydrofuran. Upon completion, the reaction mixture was stirred over weekend. After evaporation, the residue was taken up in water and the product was extracted with dichloromethane. The extract was dried, filtered and evaporated. The residue was stirred in 2,2'-oxybispropane. The precipitate was filtered off and the filtrate was evaporated. The residue was crystallized from 2-propanol, yielding 7.5 parts (38.7%) of ethyl 4-(2-pyrazinylmethoxy)benzoate; mp. 76.1° C. (interm. 9).

b) A mixture of 12.8 parts of intermediate 9 and 120 parts of ethanol was hydrogenated at normal pressure and at room temperature in the presence of 2 parts of platinum-on-charcoal catalyst 5%. After the calculated amount of hydrogen was taken up, the catalyst was filtered off over diatomaceous earth and the filtrate was evaporated, yielding 13.2 parts (100%) of ethyl 4-(2-piperazinylmethoxy)benzoate as a residue (interm. 10).

c) A mixture of 12.5 parts of intermediate 10, 5 parts of benzaldehyde, 3 parts of a thiophene solution and 200 parts of ethanol was hydrogenated at normal pressure and at room temperature in the presence of 2 parts of palladium-on-charcoal catalyst 10%. After the calculated amount of hydrogen was taken up, the catalyst was filtered off over diatomaceous earth and the filtrate was evaporated. The residue was purified by column chromatography (silica gel; $CHCl_3/C_2H_5OH$ 99.5:0.5). The eluent of the desired fraction was evaporated, yielding 11.2 parts (67.1%) of ethyl 4-[[4-(phenylmethyl)-2-piperazinyl]methoxy]benzoate as a residue (interm. 11).

d) A mixture of 6.6 parts of intermediate 11, 2 parts of poly(oxymethylene), 2 parts of a thiophene solution and 200 parts of ethanol was hydrogenated at normal pressure and at room temperature in the presence of 2 parts of palladium-on-charcoal catalyst 10%. After the calculated amount of hydrogen was taken up, the catalyst was filtered off over diatomaceous earth and the filtrate was evaporated. The residue was dissolved in dichloromethane, washed with an ammonium hydroxide solution and water, dried, filtered and evaporated, yielding 5.8 parts (84.6%) of ethyl 4-[[1-methyl-4-(phenylmethyl)-2-piperazinyl]methoxy]benzoate as a residue (interm. 12).

e) A mixture of 5.8 parts of intermediate 12 and 120 parts of ethanol was hydrogenated at normal pressure and at room temperature in the presence of 2 parts of palladium-on-charcoal catalyst 10%. After the calculated amount of hydrogen was taken up, the catalyst was filtered off over diatomaceous earth and the filtrate was evaporated, yielding 4 parts (91.5%) of ethyl 4-[(1-methyl-2-piperazinyl)methoxy]benzoate as a residue (interm. 13).

EXAMPLE 4 a) A mixture of 50 parts of 4-bromo-1-butene, 58 parts of ethyl 4-hydroxybenzoate, 55.2 parts of potassium carbonate and 320 parts of 2-propanone was refluxed for 68 hours. The reaction mixture was evaporated and the residue was dissolved in methylbenzene. The organic solution was washed with a diluted sodium hydroxide solution. The separated organic layer was dried, filtered and evaporated, yielding 25 parts (33%) of ethyl 4-(3-butenyloxy)benzoate as an oily residue (interm. 14).

b) To a stirred solution of 25.9 parts of 3-chlorobenzenecarboperoxoic acid in 260 parts of dichloromethane was added dropwise a solution of 25 parts of intermediate 14 in 65 parts of dichloromethane at 20° C. After stirring overnight at 20° C., the precipitate was filtered off and the filtrate was washed with a cold diluted sodium hydroxide solution. The separated organic layer was dried, filtered and evaporated, yielding 23.6 parts (90.8%) of ethyl 4-[2-(oxiranyl)ethoxy]benzoate as an oily residue (interm. 15).

c) A mixture of 23.6 parts of intermediate 15, 15.1 parts of 2-[(phenylmethyl)amino]ethanol and 200 parts of 2-propanol was stirred overnight at reflux temperature. The reaction mixture was evaporated and the residue was purified by column chromatography (silica gel; $CHCl_3/C_2H_5OH$ 98:2). The eluent of the desired fraction was evaporated, yielding 32 parts (82.6%) of ethyl 4-[3-hydroxy-4-[(2-hydroxyethyl)(phenylmethyl)amino]butoxy]benzoate as a residue (interm. 16).

d) A mixture of 32 parts of intermediate 16 and 200 parts of ethanol was hydrogenated at normal pressure and at room temperature in the presence of 5 parts of palladium-on-charcoal catalyst 10%. After the calculated amount of hydrogen was taken up, the catalyst was filtered off over diatomaceous earth and the filtrate was evaporated, yielding 23.8 parts (96.7%) of ethyl 4-[3-hydroxy-4-[(2-hydroxyethyl)amino]butoxy]benzoate as a residue (interm. 17).

e) A mixture of 17.2 parts of 4-methylbenzenesulfonyl chloride, 23.8 parts of intermediate 17, 21.2 parts of sodium carbonate and 282 parts of N,N-dimethylformamide was stirred overnight at ±90° C. The reaction mixture was poured into ice water. The precipitated product was filtered off, dissolved in dichloromethane, dried, filtered and evaporated, yielding 33 parts (91.4%) of ethyl 4-[3-hydroxy-4-[(2-hydroxyethyl)(4-methylphenyl)sulfonyl]amino]butoxy]benzoate as a residue (interm. 18).

f) A solution of 33 parts of intermediate 18 in 261 parts of methylbenzene was added dropwise to a solution of 47.6 parts of thionyl chloride in 0.5 parts of N,N-dimethylformamide. The reaction mixture was stirred overnight at room temperature and then for 1 hour at reflux temperature. The whole was evaporated, yielding 35 parts (98.2%) of ethyl 4-[3-chloro-4-[(2-chloroethyl)[(4-methylphenyl)sulfonyl]amino]butoxy]benzoate as a residue (interm. 19).

g) A mixture of 35 parts of intermediate 19, 36 parts of sodium sulfide nonahydrate, 0.1 parts of sulfur powder and 320 parts of ethanol was refluxed for 4 hours. The reaction mixture was evaporated and the residue was taken up in water. The whole was refluxed for 30 minutes. After cooling, the reaction mixture was treated with hydrochloric acid. The precipitated product was filtered off, dissolved in ethanol and 1.6 parts of sulfuric acid and refluxed overnight. After evaporation, the residue was taken up in ice water and extracted with dichloromethane. The extract was washed with an ammonium hydroxide solution, dried, filtered and evaporated. The residue was purified by column chromatography (silica gel; $CHCl_3/C_2H_5OH$ 99:1). The eluent of the desired fraction was evaporated, yielding 21.5 parts (66.8%) of ethyl 4-[2-[4-[(4-methylphenyl)sulfonyl]-2-thiomorpholinyl]ethoxy]benzoate as a residue (interm. 20).

h) A mixture of 21.5 parts of intermediate 20, 54 parts of 1,2-ethanediamine and 94 parts of N,N-dimethylformamide was detosylated (electrochemically) with 5 parts of N,N,N-triethylethanammonium bromide. The reaction mixture was poured into water and the product was extracted with dichloromethane. The extract was washed with water, dried, filtered and evaporated. The residue was converted into the (E)-2-butenedioate salt in 2-propanol. The salt was filtered off and dried, yielding 9.3 parts (47.3%) of ethyl 4-[2-(2-thiomorpholinyl)ethoxy]benzoate (E)-2-butenedioate(1:1); mp. 141° C. (interm. 21).

In a similar manner there was also prepared: ethyl 4-(2-thiomorpholinylmethoxy)benzoate (interm. 22).

i) 2 Parts of a sodium hydride dispersion 50% were added portionwise to a mixture of 3.6 parts of N-hydroxypropanimidamide and 135 parts of tetrahydrofuran. After stirring for 30 minutes at room temperature, a solution of 5.9 parts of intermediate 21 in 45 parts of tetrahydrofuran was added dropwise and stirring was continued first for 30 minutes at room temperature and then overnight at reflux temperature. After evaporation, the residue was taken up in ice water. The whole was stirred for 15 minutes and the aqueous layer was decanted. The residue was washed with petroleum ether, dissolved in dichloromethane, dried, filtered and evaporated, yielding 5.7 parts (89.2%) of 2-[2-[4-(3-ethyl-1,2,4-oxadiazol-5-yl)phenoxy]ethyl]thiomorpholine as a residue (interm. 23).

EXAMPLE 5 a) A mixture of 18 parts of intermediate 4 and 160 parts of methanol was hydrogenated at normal pressure and at room temperature in the presence of 2 parts of palladium-on-charcoal catalyst. After the calculated amount of hydrogen was taken up, the catalyst was filtered off over diatomaceous earth and the filtrate was evaporated, yielding 9.1 parts (86.7%) of 2-morpholineethanol as a residue (interm. 24).

b) A mixture of 4 parts of 3,6-dichloropyridazine, 2.64 parts of intermediate 24, 6.3 parts of sodium carbonate and 141 parts of N,N-dimethylformamide was stirred overnight at ±90° C. The reaction mixture was poured into water. The aqueous layer was evaporated and the residue was taken up in dichloromethane. After stirring for 1 hour, the separated organic layer was evaporated and the residue was purified by column chromatography (silica gel; $CHCl_3/CH_3OH$ 99:1). The eluent of the desired fraction was evaporated. The residue was treated twice with methylbenzene and evaporated, yielding 2.9 parts (59.5%) of 4-(6-chloro-3-pyridazinyl)-2-morpholineethanol as a residue (interm. 25).

In a similar manner there was also prepared: 4-(5-bromo-1,3,4-thiadiazol-2-yl)-2-(chloromethyl)morpholine (interm. 26).

EXAMPLE 6

To a mixture of 29.9 parts of ethyl 4-hydroxybenzoate and 316 parts of ethanol were added portionwise 35.6 parts of sodium ethoxide. After stirring for ½ hour at room temperature, there was added dropwise a solution of 31.7 parts of N-hydroxypropanimidamide in 79 parts of ethanol. Stirring was continued for ½ hour at room temperature and overnight at reflux temperature. The reaction mixture was evaporated and the residue was taken up in water. After neutralizing with acetic acid, the precipitate was filtered off and dried. It was purified by column chromatography (HPLC; silica gel; $CH_2Cl_2/CH_3OH$ 99:1). The eluent of the desired fraction was evaporated and the residue was stirred in petroleumether. The precipitate was filtered off and dried, yielding 7.56 parts (22.1%) of 4-(3-ethyl-1,2,4-oxadiazol-5-yl)phenol; mp. 137.7° C. (interm. 27).

EXAMPLE 7 a) To a cooled (5° C.) mixture of 12.9 parts of ethyl 4-[4-hydroxy-5-[(2-hydroxyethyl) (phenylmethyl)amino]pentyl]benzoate (prepared following the procedure described in Example 4 (a), (b), (c)), 7.86 parts of triphenyl phosphine and 90 parts of trichloromethane were added dropwise 7 parts of diethyl azodicarboxylate. After stirring overnight at 20° C., the reaction mixture was diluted with 50 parts of water. The organic layer was dried, filtered and evaporated. The residue was dissolved in 261 parts of methylbenzene and this solution was well mixed with 200 ml of HCl 2N. The whole was basified with ammonium hydroxide and extracted with dichloromethane. The extract was dried, filtered and evaporated and the residue was converted into the monohydrochloride salt in 2-propanol. The product was filtered off and dried, yielding 4 parts (31.7%) of ethyl 4-[3-[4-(phenylmethyl)-2-morpholinyl]propoxy]benzoate hydrochloride (interm. 28).

b) A mixture of 4 parts of intermediate 28 and 119 parts of ethanol was hydrogenated at normal pressure and room temperature with 2 parts of palladium-on-charcoal catalyst 10%. After the calculated amount of hydrogen was taken up, the catalyst was filtered off and the filtrate was evaporated, yielding 2.9 parts (87.9%) of ethyl 4-[3-(2-morpholinyl)propoxy]benzoate hydrochloride (interm. 29).

B. Preparation of the Final Compounds

EXAMPLE 8

A mixture of 3.96 parts of 2,5-dibromo-1,3,4-thiadiazole, 4 parts of intermediate 8, 5.3 parts of sodium carbonate and 94 parts of N,N-dimethylformamide was stirred overnight at 65° C. The reaction mixture was evaporated and the residue was taken up in water. The precipitate was filtered off, washed with water and dissolved in dichloromethane. The organic layer was dried, filtered and evaporated. The residue was purified by column chromatography (silica gel; $CH_2Cl_2/CH_3OH$ 99:1). The eluent of the desired fractions was evaporated and the residue was crystallized from 2-propanol. The product was filtered off and dried, yielding 2.1 parts (31.7%) of ethyl 4-[2-[4-(5-bromo-1,3,4-thiadiazol-2-yl)-2-morpholinyl]ethoxy]benzoate; mp. 130.8° C. (compound 12).

EXAMPLE 9

A mixture of 2.4 parts of 3-chloro-6-(methylthio)-pyridazine, 3.5 parts of intermediate 8, 1.6 parts of sodium carbonate and 3 drops of N,N-dimethylacetamide was stirred for 6 hours at ±160° C. The reaction mixture was allowed to stand over weekend. Water and dichloromethane were added and the separated organic layer was dried, filtered and evaporated. The residue was crystallized from a mixture of 2,2'-oxybispropane and 2-propanol. The product was filtered off and dried, yielding 2.1 parts (40%) of ethyl 4-[2-[4-[6-(methylthio)-3-pyridazinyl]-2-morpholinyl]ethoxy]benzoate; mp. 111.4° C. (compound 23).

EXAMPLE 10

A mixture of 2.6 parts of 3-chloro-1,2-benzisothiazole, 1,1-dioxide, 3 parts of intermediate 8, 5.3 parts of sodium carbonate and 120 parts of 4-methyl-2-pentanone was refluxed overnight and allowed to stand over weekend. After the addition of water, the separated organic layer was dried, filtered and evaporated. The residue was crystallized from ethanol. The product was filtered off and dried, yielding 3.3 parts (67.5%) of ethyl 4-[2-[4-(1,2-benzisothiazol-3-yl)-2-morpholinyl]ethoxy]benzoate, S,S-dioxide; mp. 150.5° C. (compound 22).

EXAMPLE 11

A mixture of 2.6 parts of 2-bromo-5-methyl-1,3,4-thiadiazole, 4.0 parts of intermediate 2 and 1.6 parts of sodium carbonate was stirred for 6 hours at 140° C. After cooling, the reaction mixture was taken up in water and dichloromethane. The separated organic layer was dried, filtered and evaporated. The residue was purified by column chromatography (silica gel; $CHCl_3/CH_3OH$ 99:1). The eluent of the desired fractions was evaporated and the residue was crystallized from 2-propanol. The product was filtered off, washed with 2-propanol and 2,2'-oxybispropane and dried at 60° C., yielding 1.3 parts (23.8%) of ethyl 4-[[4-(5-methyl-1,3,4-thiadiazol-2-yl)-2-morpholinyl]methoxy]benzoate; mp. 112.4° C. (compound 15).

EXAMPLE 12

A mixture of 2.9 parts of 3-chloro-6-(methylsulfonyl)-pyridazine, 4 parts of intermediate 2, 2 parts of N,N-diethylethanamine and 131 parts of methylbenzene was stirred for 20 hours at reflux temperature. After cooling, there were added 100 parts of water and stirring was carried on for 1 hour. The precipitate was filtered off, washed with water and dissolved in dichloromethane. This solution was dried, filtered and evaporated and the residue was crystallized from ethanol, yielding 4 parts (63.3%) of ethyl 4-[[4-[6-(methylsulfonyl)-3-pyridazinyl]-2-morpholinyl]methoxy]benzoate; mp. 196.6° C. (compound 7).

EXAMPLE 13

To a stirred and cooled (±10° C.) solution of 2.9 parts of intermediate 25, 2.3 parts of intermediate 27, 4.7 parts of triphenylphosphine in 45 parts of tetrahydrofuran was added dropwise a solution of 3.0 parts of diethyl azodicarboxylate in a small amount of tetrahydrofuran. Upon completion, stirring was continued overnight at room temperature. The precipitated product was filtered off and the filtrate was evaporated. The residue was crystallized from 2-propanol. The crystallized product was filtered off, combined with the precipitated product (see above) and crystallized from ethanol. The product was filtered off, washed with 2-propanol and dried in vacuo at 50° C., yielding 3.0 parts (60.1%) of 3-chloro-6-[2-[2-[4-(3-ethyl-1,2,4-oxadiazol-5-yl)phenoxy]ethyl]4-morpholinyl]pyridazine; mp. 164.1° C. (compound 31).

EXAMPLE 14

A mixture of 2.5 parts of compound 1, 0.5 parts of a solution of thiophene in methanol 4%, 1 part of calcium oxide and 119 parts of ethanol was hydrogenated at normal pressure and at 20° C. with 1 part of palladium-on-charcoal catalyst 10%. After the calculated amount of hydrogen was taken up, the catalyst was filtered off and the filtrate was evaporated. Water was added to the residue and the whole was basified with $NH_4OH$ (conc.). The product was extracted with dichloromethane and the extract was dried, filtered and evaporated. The residue was purified by column chromatography (silica gel; $CHCl_3/CH_3OH$ 98:2). The eluent of the desired fraction was evaporated and the residue was crystallized from a mixture of 2-propanol and 2,2'-oxybispropane, yielding 0.9 parts (39.7%) of ethyl 4-[[4-(3-pyridazinyl)-2-morpholinyl]methoxy]benzoate; mp. 110.5° C. (compound 8).

The compounds listed in Table 1 were prepared according to similar procedures as described in any of the preceding examples 8-14.

TABLE 1

Het—N⟨ring with X⟩—C$_n$H$_{2n}$—O—⟨phenyl⟩—R$^3$

| Comp. No. | Ex. No. | Het | X | n | R$^3$ | Physical data |
|---|---|---|---|---|---|---|
| 1 | 8 | 3-chloro-pyridazin-6-yl | O | 1 | COOC$_2$H$_5$ | mp. 155.2° C. |
| 2 | 11 | 3-methyl-pyridazin-6-yl | O | 1 | COOC$_2$H$_5$ | mp. 125.8° C./(Z)-2-butenedioate (1:1) |
| 3 | 8 | 3-bromo-pyridazin-6-yl | O | 1 | COOC$_2$H$_5$ | mp. 163.5° C. |
| 4 | 8 | 3-(ethoxycarbonyl)-pyridazin-6-yl | O | 1 | COOC$_2$H$_5$ | mp. 133.4° C. |
| 5 | 8 | 3-fluoro-pyridazin-6-yl | O | 1 | COOC$_2$H$_5$ | mp. 114.8° C. |
| 6 | 8 | 3-iodo-pyridazin-6-yl | O | 1 | COOC$_2$H$_5$ | mp. 164.0° C. |
| 7 | 12 | 3-(methylsulfonyl)-pyridazin-6-yl | O | 1 | COOC$_2$H$_5$ | mp. 196.6° C. |
| 8 | 14 | pyridazin-3-yl | O | 1 | COOC$_2$H$_5$ | mp. 110.5° C. |
| 9 | 12 | 3-(methylsulfinyl)-pyridazin-6-yl | O | 1 | COOC$_2$H$_5$ | mp. 160.5° C. |
| 10 | 9 | 3-(methylthio)-pyridazin-6-yl | O | 1 | COOC$_2$H$_5$ | mp. 122.1° C. |
| 11 | 8 | 3-chloro-pyridazin-6-yl | O | 2 | COOC$_2$H$_5$ | mp. 118.9° C. |

TABLE 1-continued

Structure: Het-N(piperidine with X)-C_nH_{2n}-O-C_6H_4-R^3

| Comp. No. | Ex. No. | Het | X | n | R³ | Physical data |
|---|---|---|---|---|---|---|
| 12 | 8 | Br-C(=N-N=)-S-C(CH₃) (thiadiazole, Br) | O | 2 | COOC₂H₅ | mp. 130.8° C. |
| 13 | 8 | 6-chloro-3-methylpyridazine | NH | 1 | COOC₂H₅ | mp. 153.8° C. |
| 14 | 8 | 6-chloro-3-methylpyridazine | O | 3 | COOC₂H₅ | mp. 100.5° C. |
| 15 | 11 | H₃C-thiadiazole-CH₃ | O | 1 | COOC₂H₅ | mp. 112.4° C. |
| 16 | 8 | H₂N-thiadiazole-CH₃ | O | 1 | COOC₂H₅ | mp. 165.8° C. |
| 17 | 8 | 6-bromo-3-methylpyridazine | O | 2 | COOC₂H₅ | mp. 141.1° C. |
| 18 | 8 | O₂N-thiazole-CH₃ | O | 1 | COOC₂H₅ | mp. 123.3° C. |
| 19 | 8 | H₂N-thiadiazole-CH₃ | O | 2 | COOC₂H₅ | mp. 194.4° C. |
| 20 | 8 | 6-iodo-3-methylpyridazine | O | 2 | COOC₂H₅ | mp. 156.0° C. |
| 21 | 8 | H₃C-thiadiazole-CH₃ | O | 2 | COOC₂H₅ | mp. 89.6° C. |
| 22 | 10 | benzisothiazole-S,S-dioxide | O | 2 | COOC₂H₅ | mp. 150.5° C. |
| 23 | 9 | 6-methylthio-3-methylpyridazine | O | 2 | COOC₂H₅ | mp. 111.4° C. |

TABLE 1-continued

Het-N\\_/X
   \\_/
    C_nH_{2n}—O—⟨phenyl⟩—R³

| Comp. No. | Ex. No. | Het | X | n | R³ | Physical date |
|---|---|---|---|---|---|---|
| 24 | 11 | ethyl thiazole-carboxylate (H5C2-O-C(O)- on thiazole with CH3) | O | 2 | COOC₂H₅ | mp. 99.8° C. |
| 25 | 11 | phenyl-thiadiazole-CH3 | O | 2 | COOC₂H₅ | mp.127.4° C. |
| 26 | 9 | 3,6-dimethylpyridazine | O | 2 | COOC₂H₅ | mp. 127.3° C. |
| 27 | 8 | 5-bromo-3-methyl-thiadiazole | O | 1 | COOC₂H₅ | mp. 126.7° C. |
| 28 | 8 | 5-bromo-3-methyl-thiadiazole | S | 1 | COOC₂H₅ | mp. 100.0° C. |
| 29 | 8 | 3-chloro-6-methyl-pyridazine | O | 1 | oxadiazole (CH3, C2H5) | mp. 169.3° C. |
| 30 | 8 | 3-chloro-6-methyl-pyridazine | S | 2 | COOC₂H₅ | mp. 108.3° C. |
| 31 | 13 | 3-chloro-6-methyl-pyridazine | O | 2 | oxadiazole (CH3, C2H5) | mp. 164.1° C. |
| 32 | 8 | 3-chloro-6-methyl-pyridazine | S | 2 | oxadiazole (CH3, C2H5) | mp. 114.4° C. |
| 33 | 8 | 3-chloro-6-methyl-pyridazine | NCH₃ | 1 | COOC₂H₅ | mp. 130.0° C. |
| 34 | 8 | 3-chloro-6-methyl-pyridazine | O | 2 | COOC₂H₅ | mp. 138.3° C. $[\alpha]_D^{20} = -30.74°$ |

EXAMPLE 15

The compounds listed in Table 2 are prepared according to similar procedures as described in any of the preceding examples 8-14.

TABLE 2

Het-N—⟨  ⟩—C$_n$H$_{2n}$—O—⟨phenyl⟩—C(=O)—O—CH$_2$—CH$_3$ with X substituent

| Comp. No. | Het | X | n |
|---|---|---|---|
| 35 | Cl-substituted thiazole | O | 2 |
| 36 | phenyl-vinyl-thiazole | O | 2 |
| 37 | thiadiazole | O | 2 |
| 38 | I-pyridazine (N—N) | S | 2 |
| 39 | H$_3$C—S—pyridazine (N—N) | S | 2 |

C. Biological Examples

The strong antiviral activity of the compounds of formula (I) is clearly evidenced by the data obtained in the following experiment, which data are only given to illustrate the useful antiviral properties of all the compounds of formula (I) and not to limit the invention either with respect to the scope of susceptible viruses nor with respect to the scope of formula (I).

EXAMPLE 16: Picornavirus Minimal Inhibitory Concentration Test

The Minimal Inhibitory Concentration of the compounds of the present invention against the Human Rhinovirus strains (HRV) -2,-9,-14,-15,-29,-39,-41,-42,-45,-51,-59,-63,-70,-72,-85,-86,-89 was determined by a standard cytopathic effect reduction assay as follows. To each of the ninty six (96) wells of a microtiter 96 well tissue culture plate there was added 60 μl of a Ohio Hela cell maintenance medium [Eagle's Basal medium supplemented with 5% Foetal Calf Serum (FCS)]. To two wells there was added 60 μl of an appropriate starting dilution of a compound of formula (I) and two-fold dilutions were made to cover a wide range of compound concentrations. Subsequently there were added 120 μl of an infectious solution of virus in Eagle's Basal Medium with 2% Hepes buffer, 2% FCS and 30 mM MgCl$_2$ to all wells except cell and compound controls. Said infectious virus solution having a TCID$_{50}$-value (Tissue Culture Infectious Dose) of about 100.

The TCID$_{50}$-value is the dose of viruses which initiates a cytopathic effect in 50% of the inoculated cells. 150 μl of the thus obtained virus-compound mixtures were then transferred to microtitre plates with subconfluent Ohio Hela Cells, grown in 100 μl of maintenance medium. Appropriate virus controls, cell controls and compound controls were included in each test. Plates were incubated for 3 to 5 days at 33° C. in 5% CO$_2$ atmosphere. They were checked daily by light microscopy without staining and read when the virus controls showed 100% cytopathic effect (CPE) and the virus back titration confirmed that a TCID$_{50}$-value between 32 and 256 had been used in the test. The IC$_{50}$-value for each virus-compound series was taken as the concentration in ng/ml that protected 50% of the cells from cytopathic effects with respect to the untreated controls. In the standard test procedure, the compounds were tested against two panels of rhinoviruses, a first panel consisting of serotypes HRV -2,-29,-39,-85,-9,-15,-51,-59,-63,-89,-41 and the other panel consisting of HRV -42,-45,-14,-70,-72 and -86.

The IC$_{50}$-value for each rhinovirus serotype was determined, and the efficacy of each compound was determined in terms of the Med$_1$-value and Med$_2$-value, which is the medium value of the IC$_{50}$-values of all serotypes from the first and second panel respectively.

The following table gives the testing results with some compounds of the invention.

| Activity of antirhinoviral compounds | | |
|---|---|---|
| Comp. No. | Med$_1$(ng/ml) | Med$_2$(ng/ml) |
| 11 | 6 | 29 |
| 17 | 2 | 22 |
| 20 | 2 | 12 |
| 21 | 6 | 21 |
| 23 | 3 | 12 |
| 26 | 5 | 29 |

We claim:

1. A compound of the formula

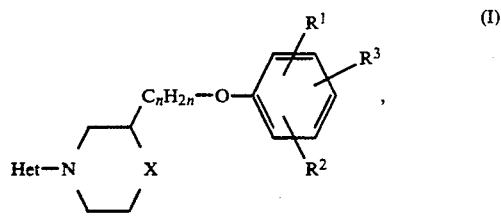

(I)

a pharmaceutically acceptable addition salt thereof or a stereochemically isomeric form thereof, wherein Het is a heterocycle of formula

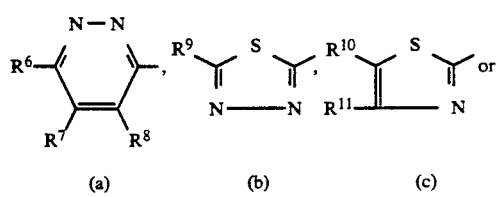

(a)      (b)      (c)

-continued

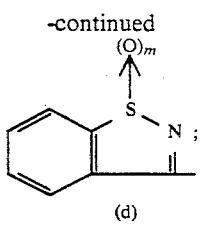
(d)

$R^6$ is hydrogen, $C_{1-4}$alkyl, halo, hydroxy, trifluoromethyl, cyano, $C_{1-4}$alkyloxy, $C_{1-4}$alkylthio, $C_{1-4}$alkylsulfinyl, $C_{1-4}$alkylsulfonyl, $C_{1-4}$alkyloxycarbonyl, $C_{1-4}$alkylcarbonyl or aryl;

$R^7$ and $R^8$ each independently are hydrogen or $C_{1-4}$alkyl;

$R^9$ is hydrogen, halo, amino, $C_{1-4}$alkyl, trifluoromethyl or aryl;

$R^{10}$ is hydrogen, halo, amino or nitro;

$R^{11}$ is hydrogen, $C_{1-4}$alkyl, $C_{1-4}$alkyloxycarbonyl or aryl;

m is 0, 1 or 2;

X is O;

n is an integer of from 1 to 4 inclusive;

$R^1$ and $R^2$ each independently are hydrogen, $C_{1-4}$alkyl or halo; and $R^3$ is hydrogen, halo, cyano, $C_{1-4}$alkyloxy, aryl or —COOR$^4$ with $R^4$ being hydrogen, $C_{1-4}$alkyl, aryl$C_{1-4}$alkyl, $C_{3-6}$cycloalkyl$C_{1-4}$alkyl, $C_{3-5}$alkenyl, $C_{3-5}$alkynyl or $C_{1-4}$alkyloxy$C_{1-4}$alkyl; or $R^3$ is a radical of formula

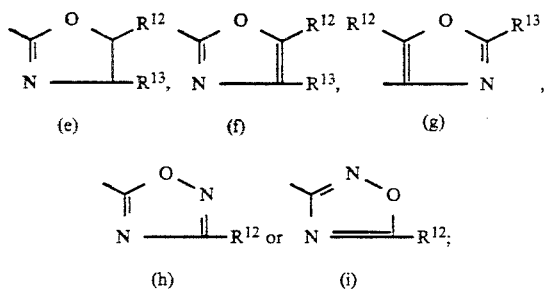

$R^{12}$ and $R^{13}$ each independently are hydrogen, $C_{1-4}$alkyl, aryl or aryl$C_{1-4}$alkyl;

wherein each aryl is phenyl, optionally substituted with 1 or 2 substituents each independently selected from halo, $C_{1-4}$alkyl, trifluoromethyl, $C_{1-4}$alkyloxy or hydroxy.

2. A compound according to claim 1 wherein Het is a radical of formula (a) wherein $R^6$ represents hydrogen, $C_{1-4}$alkyl, $C_{1-4}$alkylthio, halo, $C_{1-4}$alkylsulfinyl or $C_{1-4}$alkylsulfonyl, and $R^7$ and $R^8$ are both hydrogen; or a radical of formula (b) wherein $R^9$ represents hydrogen, halo, $C_{1-4}$alkyl, amino or aryl; or a radical of formula (c) wherein $R^{10}$ represents hydrogen, halo or nitro and $R^{11}$ represents hydrogen or $C_{1-4}$alkyloxycarbonyl; or a radical of formula (d) wherein m is 2.

3. A compound according to claim 2 wherein $R^1$ and $R^2$ each independently are hydrogen or halo; $R^3$ is a radical of formula —COOR$^4$ wherein $R^4$ represents $C_{1-4}$alkyl, $C_{3-5}$alkenyl, $C_{3-5}$alkynyl or $C_{1-4}$alkyloxy$C_{1-4}$alkyl, or $R^3$ is a heterocycle of formula (e), (f), (g), (h) or (i) wherein $R^{12}$ and $R^{13}$ each independently represent hydrogen or $C_{1-4}$alkyl.

4. A compound according to claim 3 wherein Het is a radical of formula (a) wherein $R^6$ represents $C_{1-4}$alkyl, halo or $C_{1-4}$alkylthio, or a radical of formula (b) wherein $R^9$ represents $C_{1-4}$alkyl or halo; $R^1$ and $R^2$ are both hydrogen; $R^3$ is $C_{1-4}$alkyloxycarbonyl or a 1,2,4-oxadiazol-5-yl of formula (h) with $R^{12}$ being $C_{1-4}$alkyl; and n is 1, 2 or 3.

5. A compound according to claim 4 wherein Het is a radical of formula (a) wherein $R^6$ represents methyl, chloro, bromo, iodo or methylthio, or a radical of formula (b) wherein $R^9$ represents methyl, chloro, bromo or iodo; and n is 1 or 2.

6. A compound according to claim 5 wherein Het is a radical of formula (a) wherein $R^6$ represents iodo, bromo or methylthio or a radical of formula (b) wherein $R^9$ represents methyl or bromo; n is 2; and $R^3$ is methoxycarbonyl, ethoxycarbonyl or 3-ethyl-1,2,4-oxadiazol-5-yl.

7. A compound according to claim 1 wherein the compound is ethyl 4-[2-[4-(6-iodo-3-pyridazinyl)-2-morpholinyl]ethoxy]benzoate or ethyl 4-[2-[4-[6-(methylthio)-3-pyridazinyl]-2-morpholinyl]ethoxy]benzoate.

8. A method of inhibiting, combating or preventing the growth of picornaviruses in warm-blooded animals by the systemic or topical administration of an anti-picornavirally effective amount of a compound of formula (I) as claimed in claim 1.

9. A method according to claim 8 wherein Het is a radical of formula (a) wherein $R^6$ represents hydrogen, $C_{1-4}$alkyl, $C_{1-4}$alkylthio, halo, $C_{1-4}$alkylsulfinyl or $C_{1-4}$alkylsulfonyl, and $R^7$ and $R^8$ are both hydrogen; or a radical of formula (b) wherein $R^9$ represents hydrogen, halo, $C_{1-4}$alkyl, amino or aryl; or a radical of formula (c) wherein $R^{10}$ represents hydrogen, halo or nitro and $R^{11}$ represents hydrogen or $C_{1-4}$alkyloxycarbonyl; or a radical of formula (d) wherein m is 2.

10. A method according to claim 9 wherein $R^1$ and $R^2$ each independently are hydrogen or halo; $R^3$ is a radical of formula —COOR$^4$ wherein $R^4$ represents $C_{1-4}$alkyl, $C_{3-5}$alkenyl, $C_{3-5}$alkynyl or $C_{1-4}$alkyloxy$C_{1-4}$alkyl, or $R^3$ is a heterocycle of formula (e), (f), (g), (h) or (i) wherein $R^{12}$ and $R^{13}$ each independently represent hydrogen or $C_{1-4}$alkyl.

11. A method according to claim 10 wherein Het is a radical of formula (a) wherein $R^6$ represents $C_{1-4}$alkyl, halo or $C_{1-4}$alkylthio, or a radical of formula (b) wherein $R^9$ represents $C_{1-4}$alkyl or halo; $R^1$ and $R^2$ are both hydrogen; $R^3$ is $C_{1-4}$alkyloxycarbonyl or a 1,2,4-oxadiazol-5-yl of formula (h) with $R^{12}$ being $C_{1-4}$alkyl; and n is 1, 2 or 3.

12. A method according to claim 11 wherein Het is a radical of formula (a) wherein $R^6$ represents methyl, chloro, bromo, iodo or methylthio, or a radical of formula (b) wherein $R^9$ represents methyl, chloro, bromo or iodo; and n is 1 or 2.

13. A method according to claim 8 wherein the compound is ethyl 4-[2-[4-(6-iodo-3-pyridazinyl)-2-morpholinyl]ethoxy]benzoate or ethyl 4-[2-[4-[6-(methylthio)-3-pyridazinyl]-2-morpholinyl]ethoxy]benzoate.

14. An anti-picornaviral composition comprising an inert carrier and, if desired, other additives, and as active ingredient an anti-picornavirally effective amount of a compound of formula (I) as claimed in claim 1.

15. A composition according to claim 14 wherein Het is a radical of formula (a) wherein $R^6$ represents hydrogen, $C_{1-4}$alkyl, $C_{1-4}$alkylthio, halo, $C_{1-4}$alkylsulfinyl or $C_{1-4}$alkylsulfonyl, and $R^7$ and $R^8$ are both hydrogen; or a radical of formula (b) wherein $R^9$ represents hydrogen, halo, $C_{1-4}$alkyl, amino or aryl; or a radical of formula (c) wherein $R^{10}$ represents hydrogen, halo or nitro and $R^{11}$ represents hydrogen or $C_{1-4}$alkyloxycarbonyl; or a radical of formula (d) wherein m is 2.

16. A composition according to claim 15 wherein $R^1$ and $R^2$ each independently are hydrogen or halo; $R^3$ is a radical of formula —COOR$^4$ wherein $R^4$ represents $C_{1-4}$alkyl, $C_{3-5}$alkenyl, $C_{3-5}$alkynyl or $C_{1-4}$alkyloxy$C_{1-4}$alkyl, or $R^3$ is a heterocycle of formula (e), (f), (g), (h) or (i) wherein $R^{12}$ and $R^{13}$ each independently represent hydrogen or $C_{1-4}$alkyl.

17. A composition according to claim 16 wherein Het is a radical of formula (a) wherein $R^6$ represents $C_{1-4}$alkyl, halo or $C_{1-4}$alkylthio, or a radical of formula (b) wherein $R^9$ represents $C_{1-4}$alkyl or halo; $R^1$ and $R^2$ are both hydrogen; $R^3$ is $C_{1-4}$alkyloxycarbonyl or a 1,2,4-oxadiazol-5-yl of formula (h) with $R^{12}$ being $C_{1-4}$alkyl; and n is 1, 2 or 3.

18. A composition according to claim 17 wherein Het is a radical of formula (a) wherein $R^6$ represents methyl, chloro, bromo, iodo or methylthio, or a radical of formula (b) wherein $R^9$ represents methyl, chloro, bromo or iodo; and n is 1 or 2.

19. A composition according to claim 18 wherein Het is a radical of formula (a) wherein $R^6$ represents iodo, bromo or methylthio or a radical of formula (b) wherein $R^9$ represents methyl or bromo; n is 2; and $R^3$ is methoxycarbonyl, ethoxycarbonyl or 3-ethyl-1,2,4-oxadiazol-5-yl.

20. A composition according to claim 14 wherein the compound is ethyl 4-[2-[4-(6-iodo-3-pyridazinyl)-2-morpholinyl]ethoxy]benzoate or ethyl 4-[2-[4-[6-(methylthio)-3-pyridazinyl]-2-morpholinyl]ethoxy]benzoate.

21. A composition according to any of claims 14 to 20 further comprising a cyclodextrin or a derivative thereof.

22. A method according to claim 12 wherein Het is a radical of formula (a) wherein $R^6$ represents iodo, bromo, or methylthio.

23. A method according to claim 12 wherein Het is a radical of formula (b) wherein $R^9$ represents methyl or bromo, n is 2, and $R^3$ is methoxycarbonyl, ethoxycarbonyl, or 3-ethyl-1,2,4-oxadiazol-5-yl.

* * * * *